(12) United States Patent  
Sone

(10) Patent No.: US 9,097,850 B2  
(45) Date of Patent: Aug. 4, 2015

(54) ENDOSCOPE OBJECTIVE LENS

(71) Applicant: Olympus Medical Systems Corp., Tokyo (JP)

(72) Inventor: Nobuhiko Sone, Tokyo (JP)

(73) Assignee: OLYMPUS MEDICAL SYSTEM CORP., Tokyo (JP)

( * ) Notice: Subject to any disclaimer, the term of this patent is extended or adjusted under 35 U.S.C. 154(b) by 0 days.

(21) Appl. No.: 14/195,180

(22) Filed: Mar. 3, 2014

(65) Prior Publication Data

US 2014/0233110 A1     Aug. 21, 2014

Related U.S. Application Data

(63) Continuation of application No. PCT/JP2013/072621, filed on Aug. 23, 2013.

(30) Foreign Application Priority Data

Sep. 18, 2012    (JP) .................................. 2012-204391

(51) Int. Cl.  
*G02B 9/14*     (2006.01)  
*A61B 1/00*     (2006.01)  
(Continued)

(52) U.S. Cl.  
CPC .............. *G02B 9/14* (2013.01); *A61B 1/00188* (2013.01); *G02B 23/2438* (2013.01); *G02B 15/173* (2013.01)

(58) Field of Classification Search  
CPC .... G02B 13/0035–13/0045; G02B 9/34–9/36; A61B 1/00188; A61B 1/00174; A61B 1/00177; A61B 1/00179; A61B 1/00186; A61B 1/00183; A61B 1/0019; A61B 1/00096

USPC ......... 359/682, 686–690, 713–716, 733–735, 359/738–740, 749, 751–758, 763–766, 359/771–774, 784; 600/175–176  
See application file for complete search history.

(56) References Cited

U.S. PATENT DOCUMENTS 6,362,925 B1    3/2002  Nakamura et al.  
2007/0206293 A1    9/2007  Takato  
(Continued)

FOREIGN PATENT DOCUMENTS

EP          2 149 809        2/2010  
JP          06-317744       11/1994  
(Continued)

*Primary Examiner* — Thomas K Pham  
*Assistant Examiner* — Marin Pichler  
(74) *Attorney, Agent, or Firm* — Kenyon & Kenyon LLP

(57) ABSTRACT

Manufacturing errors are suppressed, a variable magnification function is provided, and good observation with aberrations appropriately corrected is performed. Provided is an endoscope objective lens including, in order from an object side, a positive first lens group, a negative second lens group, and a positive third lens group, in which the first lens group has a meniscus lens; and a normal observation state (wide angle end) and a magnifying observation state (telephoto end) can be switched between by moving the second lens group on the optical axis, and the following conditions are satisfied;

$$-9 < f_2/f_W < -3.5$$

$$4.5 < |f_M/f_W| < 8.3$$

where $f_M$ represents the focal distance of the meniscus lens, $f_W$ represents the entire focal distance for the normal observation, and $f_2$ represents the focal distance of the second lens group.

5 Claims, 25 Drawing Sheets

(51) Int. Cl.
*G02B 23/24* (2006.01)
*G02B 15/173* (2006.01)

(56) References Cited

U.S. PATENT DOCUMENTS

| | | | |
|---|---|---|---|
| 2007/0258150 A1 | 11/2007 | Takato | |
| 2010/0020408 A1 | 1/2010 | Noguchi | |
| 2010/0315545 A1* | 12/2010 | Tamura | 348/349 |
| 2011/0235192 A1* | 9/2011 | Uzawa et al. | 359/785 |

FOREIGN PATENT DOCUMENTS

| | | |
|---|---|---|
| JP | 2001-141996 | 5/2001 |
| JP | 2007-233036 | 9/2007 |
| JP | 2007-260305 | 10/2007 |
| JP | 2009-294496 | 12/2009 |
| JP | 2010-032680 | 2/2010 |
| JP | 4659645 | 3/2011 |
| JP | 2012-032576 | 2/2012 |

* cited by examiner

ENDOSCOPE OBJECTIVE LENS

CROSS-REFERENCE TO RELATED APPLICATIONS

This is a continuation of International Application PCT/JP2013/072621, with an international filing date of Aug. 23, 2013, which is hereby incorporated by reference herein in its entirety. This application claims the benefit of Japanese Patent Application No. 2012-204391, the content of which is incorporated herein by reference.

TECHNICAL FIELD

The present invention relates to an endoscope objective lens, in particular, to an endoscope variable-magnification objective lens that is used for an endoscope capable of performing magnifying observation in addition to normal observation.

BACKGROUND ART

In recent years, endoscopes (objective lenses) capable of performing magnifying observation have been in high demand in the medical field in order to make accurate diagnoses of lesions. Magnifying observation with an endoscope is performed such that some lenses in the objective lens are moved to change the focal distance, thus changing the observation distance. For example, when the endoscope is focused at a distance of about 5 mm for normal observation, the lenses are moved to change the focal distance, thereby making it possible to focus the endoscope at a distance of up to about 2 mm. As a result, by changing the focal distance from 5 mm to 2 mm, an object can be observed in magnified form, thus allowing magnifying observation. This configuration of lenses is generally called a focusing lens, which is different from zoom lenses that are used in cameras.

As such endoscope objective lenses capable of performing magnifying observation, endoscope optical systems that have a configuration formed of three lens groups, namely, positive, negative, and positive lens groups, and that move the second lens group, thereby performing variable magnification and focusing, are disclosed in PTLs 1 and 2.

CITATION LIST

Patent Literature

{PTL 1} Publication of Japanese Patent No. 4659645
{PTL 2} Japanese Unexamined Patent Application, Publication No. 2012-32576

SUMMARY OF INVENTION

Technical Problem

In both of the endoscope optical systems disclosed in PTLs 1 and 2, magnifying observation is allowed by moving the second lens group; however, the power of the second lens group is high, and a change in magnification with respect to the lens movement distance is large. Therefore, for magnifying observation, although the magnification can be ensured, the depth of field is narrowed; or although the depth of field can be ensured, the magnification does not reach a desired level.

The present invention provides an endoscope objective lens for which manufacturing errors are suppressed, that is provided with a variable magnification function, and that can perform good observation with aberrations appropriately corrected.

Solution to Problem

The present invention provides the following solutions.

According to one aspect, the present invention provides an endoscope objective lens including, in order from an object side, a positive first lens group, a negative second lens group, and a positive third lens group, in which the first lens group has a meniscus lens; and a normal observation state (wide angle end) and a magnifying observation state (telephoto end) can be switched between by moving the second lens group on an optical axis, and the following conditions are satisfied;

$$-9 < f_2/f_W < -3.5 \quad (1)$$

$$4.5 < |f_M/f_W| < 8.3 \quad (2)$$

where $f_M$ represents a focal distance of the meniscus lens, $f_W$ represents an entire focal distance for the normal observation, and $f_2$ represents a focal distance of the second lens group.

In the above-described aspect, the second lens group may consist of a joined lens that is formed of a concave lens having a high refractive index and a convex lens having a low refractive index; and a lens surface of the second lens group that is located closest to an object and a lens surface thereof that is located closest to an image may each have a planar shape.

In the above-described aspect, an aperture stop that is moved together with the second lens group may be further included.

In the above-described aspect, the following conditional expression may be satisfied;

$$-0.77 < f_3/f_2 < -0.34 \quad (3)$$

where $f_3$ represents a focal distance of the third lens group.

In the above-described aspect, the following conditional expression may be satisfied;

$$-4.5 < f_2/f_1 < -2.38 \quad (4)$$

where $f_1$ represents a focal distance of the first lens group.

In the above-described aspect, the following conditional expression may be satisfied;

$$1.5 < f_3/f_1 < 2.5 \quad (5).$$

DESCRIPTION OF EMBODIMENT

An endoscope objective lens according to one embodiment of the present invention will be described below with reference to the drawings.

Figure 1:
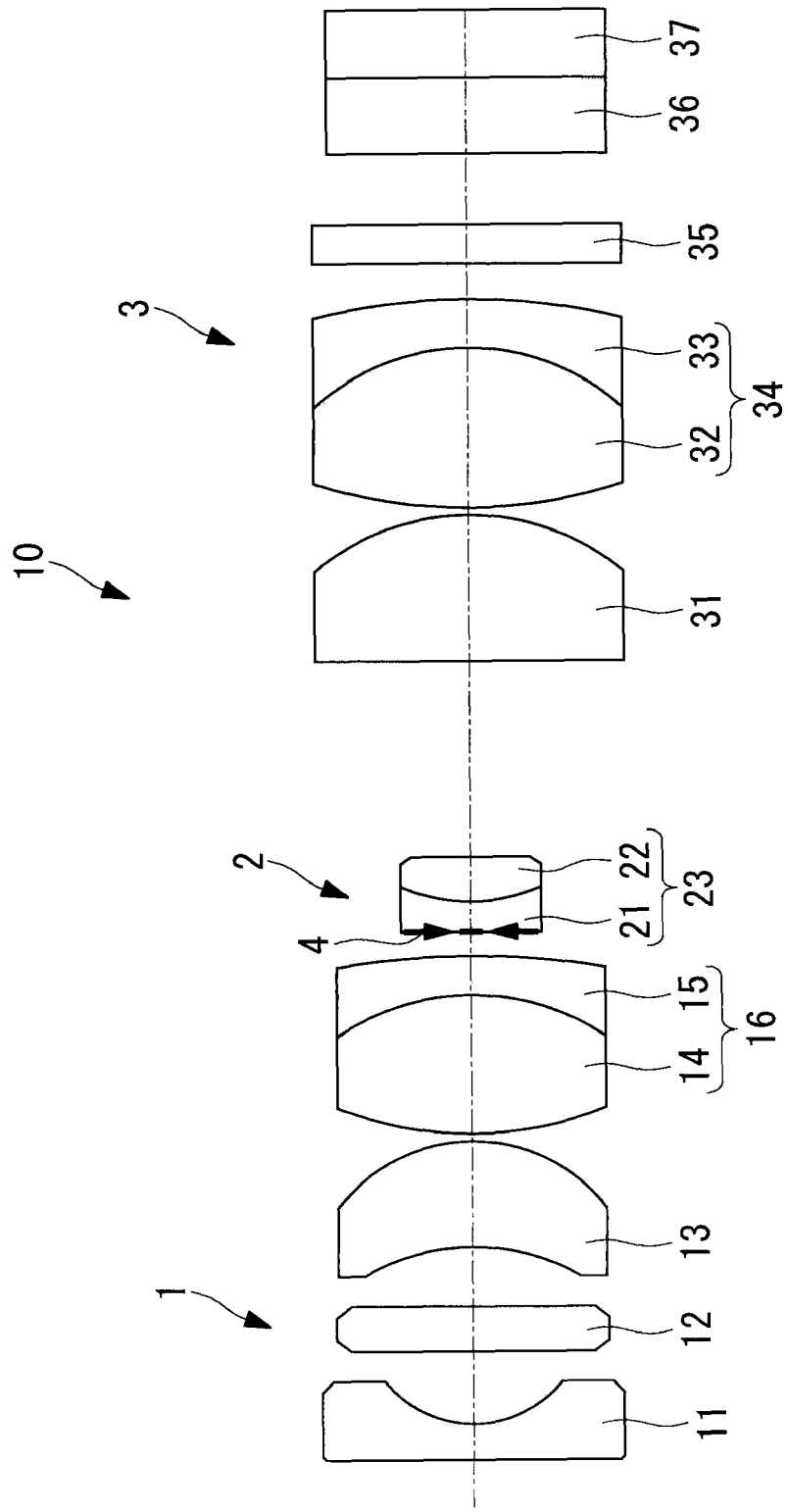
FIG. 1 is a view showing, in outline, the configuration of a normal observation state of an endoscope objective lens according to one embodiment of the present invention.
Figure 2:
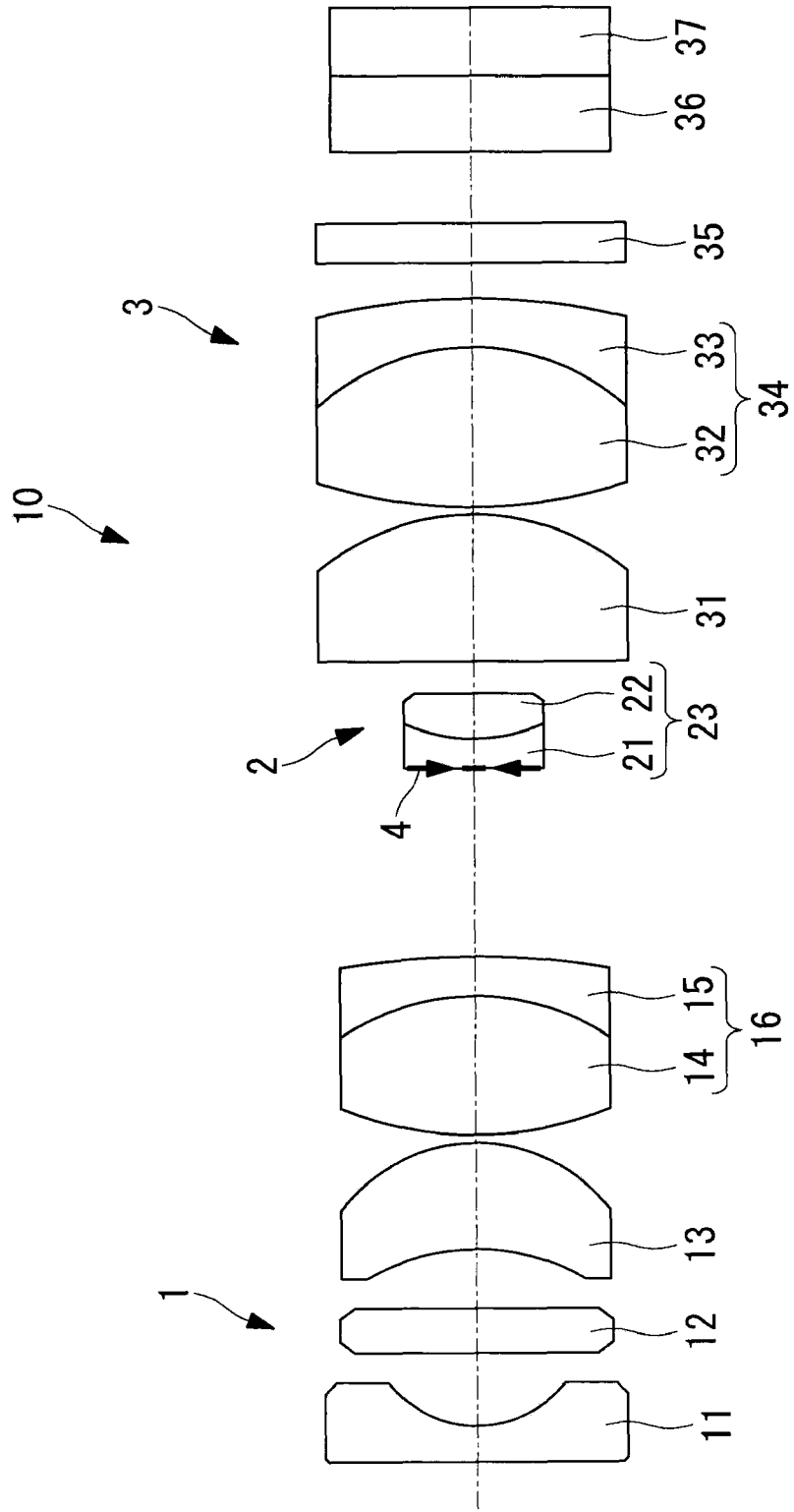
FIG. 2 is a view showing, in outline, the configuration of a magnifying observation state of the endoscope objective lens according to the embodiment of the present invention.

As shown in FIGS. 1 and 2, an endoscope objective lens 10 of this embodiment includes, in order from the object side, a positive first lens group 1, an aperture stop 4, a negative second lens group 2, and a positive third lens group 3.

The first lens group 1 consists of, in order from the object side, a planoconcave lens 11 whose flat surface faces the object side, a parallel plate 12, a meniscus lens 13 whose concave surface faces the object side, and a joined lens 16 that is formed of a biconvex lens 14 and a concave lens 15.

The second lens group 2 consists of a joined lens 23 that is formed of a concave lens 21 having a high refractive index and a convex lens 22 having a low refractive index. A lens surface (r10 shown in FIG. 3) of the second lens group 2 that is located closest to an object and a lens surface (r12 shown in FIG. 3) thereof that is located closest to an image each have a planar shape.

The third lens group 3 consists of a planoconvex lens 31 whose flat surface faces the object side; a joined lens 34 that is formed of a biconvex lens 32 and a concave lens 33; and three parallel plates 35, 36, and 37.

The second lens group 2 of this embodiment is provided so as to be capable of being moved on an optical axis together with the aperture stop 4. For example, the joined lens 23 (movable lens group), which is formed of the concave lens 21 and the convex lens 22, is held by a lens frame (not shown), and an actuator (movement mechanism, not shown) for giving a driving force to the lens frame is connected to the lens frame. Then, the joined lens 23 is moved on the optical axis together with the lens frame through actuation of the actuator.

Aside from eccentricity and tilt caused by a clearance between the lenses and the lens frame, eccentricity and tilt are caused by a clearance between the actuator (movement mechanism) and the lens frame. Therefore, the levels of eccentricity and tilt caused in the lenses of the second lens group 2, to which the movement mechanism is connected, are increased compared with those caused in the lenses of the first lens group 1 and in the lenses of the third lens group 3, to which a movement mechanism is not connected.

When eccentricity and tilt are increased, aberrations become worse, thus degrading the performance; therefore, it is desirable to provide a configuration for reducing the effects of eccentricity and tilt caused by the lenses and the lens frame. Thus, the second lens group 2 is made to consist of the joined lens 23, which is formed of the concave lens 21 having a high refractive index and the convex lens 22 having a low refractive index, thereby forming it into a parallel plate shape as a whole; therefore, it is possible to hamper the occurrence of eccentricity and tilt and to exert a negative refractive index as power.

In order to reduce the load imposed on the movement mechanism, it is desirable that the second lens group 2 have a small lens diameter. With a small diameter, processing for a meniscus lens is difficult, and the cost tends to be increased, as a result. Therefore, it is desirable to provide the configuration of the second lens group 2 of this embodiment.

The endoscope objective lens 10 can be switched between a normal observation state (wide angle end) and a magnifying observation state (telephoto end) by moving the second lens group 2 on the optical axis in the axial direction. For example, the endoscope objective lens 10 enters the normal observation state when the second lens group 2 is moved on the optical axis toward the object, as shown in FIG. 1, and enters the magnifying observation state when the second lens group 2 is moved on the optical axis toward the image, as shown in FIG. 2.

For the normal observation and the magnifying observation, it is difficult to ensure the depth of field especially when a CCD having a large number of pixels is used. Therefore, in many cases, the f-number is increased as much as possible to narrow the aperture stop 4 close to the diffraction limit, thereby ensuring the depth of field. However, in an optical system in which a lens group is moved, especially in an optical system having a positive-negative-positive configuration, the f-number for the normal observation becomes small, thus making it difficult to ensure a sufficient depth of field. Therefore, by moving the aperture stop 4 and the second lens group 2 at the same time, it is possible to reduce a change in f-number between the normal observation and the magnifying observation.

In this embodiment, the endoscope objective lens 10 satisfies the following conditional expressions;

$$-9 < f_2/f_W < -3.5 \quad (1)$$

$$4.5 < |f_M/f_W| < 8.3 \quad (2)$$

where $f_M$ represents the focal distance of the meniscus lens 13, $f_W$ represents the entire focal distance for the normal observation, and $f_2$ represents the focal distance of the second lens group 2.

Expression (1) relates to the position adjustment sensitivity of the second lens group 2. If the value of $f_2/f_W$ falls below the lower limit of Expression (1), manufacturing errors are increased. If the position adjustment sensitivity is high, the deviation from the designed objective lens is greater, thus causing a problem in that, although the magnification can be ensured, the depth of field is narrowed or a problem in that, although the depth of field can be ensured, the magnification does not reach a desired level, for example. On the other hand, if the value of $f_2/f_W$ exceeds the upper limit of Expression (1), the position adjustment sensitivity is relaxed, but it becomes difficult to ensure sufficient magnification.

The following expression is more preferable than Expression (1).

$$-8 < f_2/f_W < -4$$

Expression (2) relates to successful correction of the aberrations, in particular, chromatic aberration of magnification. If the value of $|f_M/f_W|$ falls below the lower limit of Expression (2), the lens focal distance is reduced, which leads to excessive correction of the chromatic aberration of magnification, as a result. On the other hand, if the value of $|f_M/f_W|$ exceeds the upper limit of Expression (2), the focal distance is increased, which leads to insufficient correction.

The following expression is more preferable than Expression (2).

$$5 < |f_M/f_W| < 30$$

Furthermore, the endoscope objective lens 10 satisfies the following conditional expression;

$$-0.77 < f_3/f_2 < -0.34 \quad (3)$$

where $f_3$ represents the focal distance of the third lens group 3.

If the value of $f_3/f_2$ falls below the lower limit of Expression (3), the focal distance of the third lens group 3 is increased, which increases the backfocus of the optical system. As a result, the overall length of the optical system is increased, which causes an increase in size. On the other hand, if the value of $f_3/f_2$ exceeds the upper limit of Expression (3), the aberrations in the third lens group 3, in particular, chromatic aberration of magnification, cannot be sufficiently corrected, which causes image degradation due to color blurring. Therefore, it is desirable to satisfy Expression (3).

The following expression is more preferable than Expression (3).

$$-0.7 < f_3/f_2 < -0.4$$

Furthermore, the endoscope objective lens 10 satisfies the following conditional expression;

$$-4.5 < f_2/f_1 < -2.38 \quad (4)$$

where $f_1$ represents the focal distance of the first lens group 1.

If the value of $f_2/f_1$ falls below the lower limit of Expression (4), the focal distance of the first lens group 1 is reduced, and increased spherical aberration occurs, thus making it difficult to acquire an excellent image. On the other hand, if the value of $f_2/f_1$ exceeds the upper limit of Expression (4), the focal distance of the first lens group 1 is increased, and the outer diameter of the lens in the first lens group 1, in particular, the first lens 11 closest to the object, is increased, thus increasing the tip diameter of the endoscope. Therefore, it is desirable to satisfy Expression (4).

The following expression is more preferable than Expression (4).

$$-4 < f_2/f_1 < -3$$

Furthermore, the endoscope objective lens 10 satisfies the following conditional expression.

$$1.5 < f_3/f_1 < 2.5 \quad (5)$$

If the value of $f_3/f_1$ falls below the lower limit of Expression (5), as in Expression (4), the focal distance of the first lens group 1 is increased, thus making it difficult to correct the spherical aberration. Furthermore, the comatic aberration cannot be corrected. On the other hand, if the value of $f_3/f_1$ exceeds the upper limit of Expression (5), the focal distance of the third lens group 3 is increased, thus making it difficult to correct the field curvature. If a large field curvature is caused, the resolving power is different between the center of an image and an edge thereof, thus making it difficult to acquire an excellent image. Therefore, it is desirable to satisfy Expression (5).

The following expression is more preferable than Expression (5).

$$1.6 < f_3/f_1 < 2.0$$

EXAMPLES

Next, examples of the endoscope objective lens 10 of the embodiment of the present invention will be described below with reference to the drawings.

Example 1 of Present Invention

Figure 3:
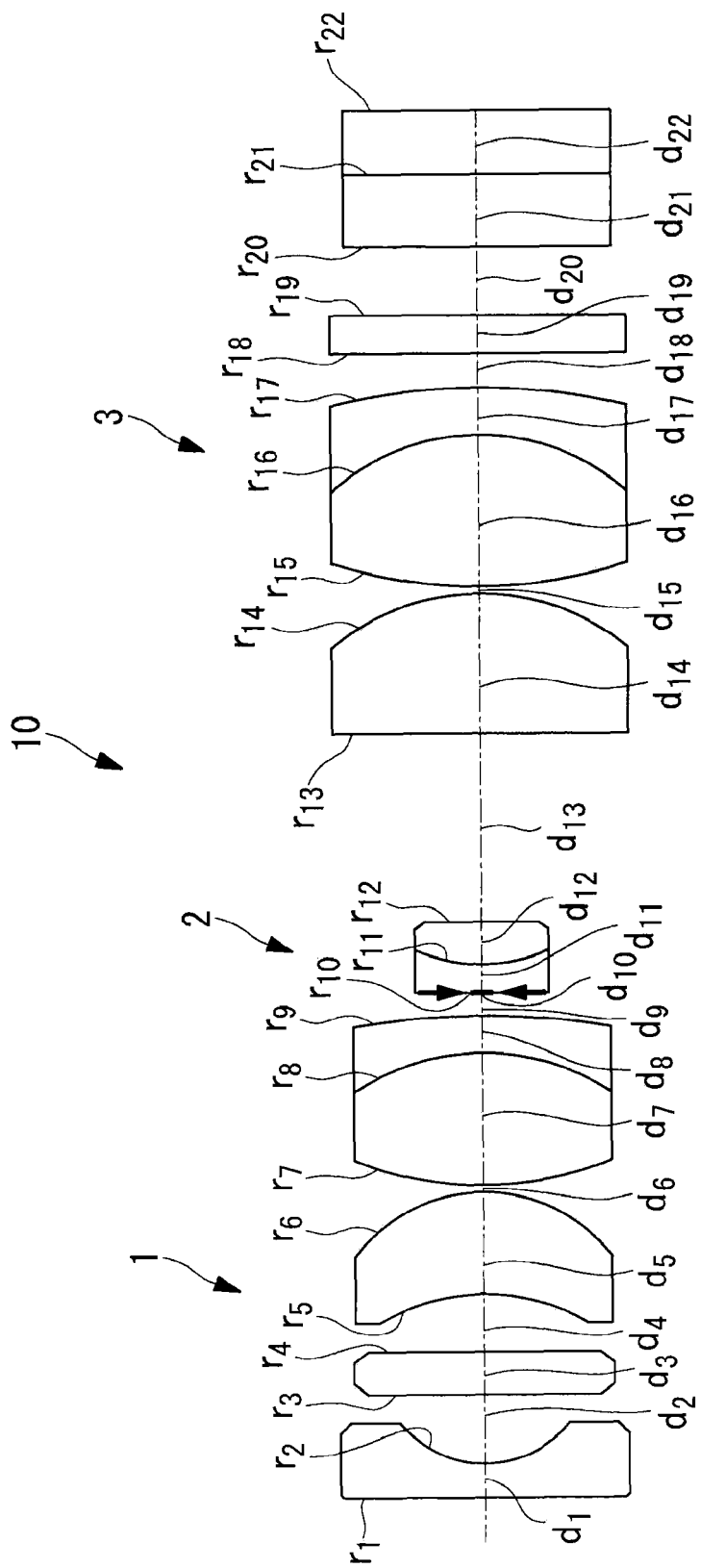
FIG. 3 is a view showing the normal observation state of an endoscope objective lens according to Example 1 of the embodiment of the present invention.
Figure 4:
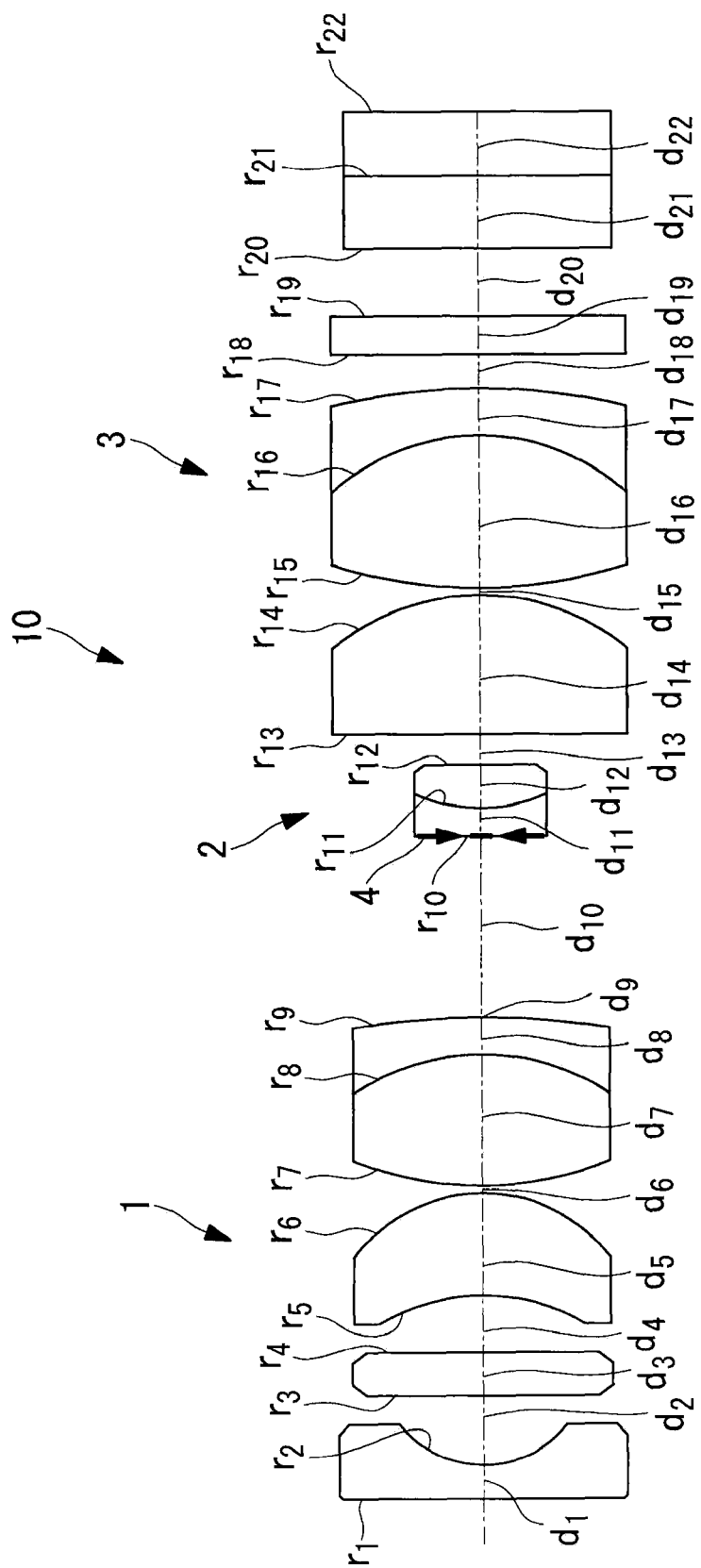
FIG. 4 is a view showing the magnifying observation state of the endoscope objective lens according to Example 1 of the embodiment of the present invention.

An endoscope objective lens 10 according to Example 1 of the present invention is shown in FIGS. 3 and 4. FIG. 3 shows a state in which the second lens group 2 has been moved toward the object, that is, a normal observation state. FIG. 4 shows a state in which the second lens group 2 has been moved toward the image, that is, a magnifying observation state.

Figure 5:
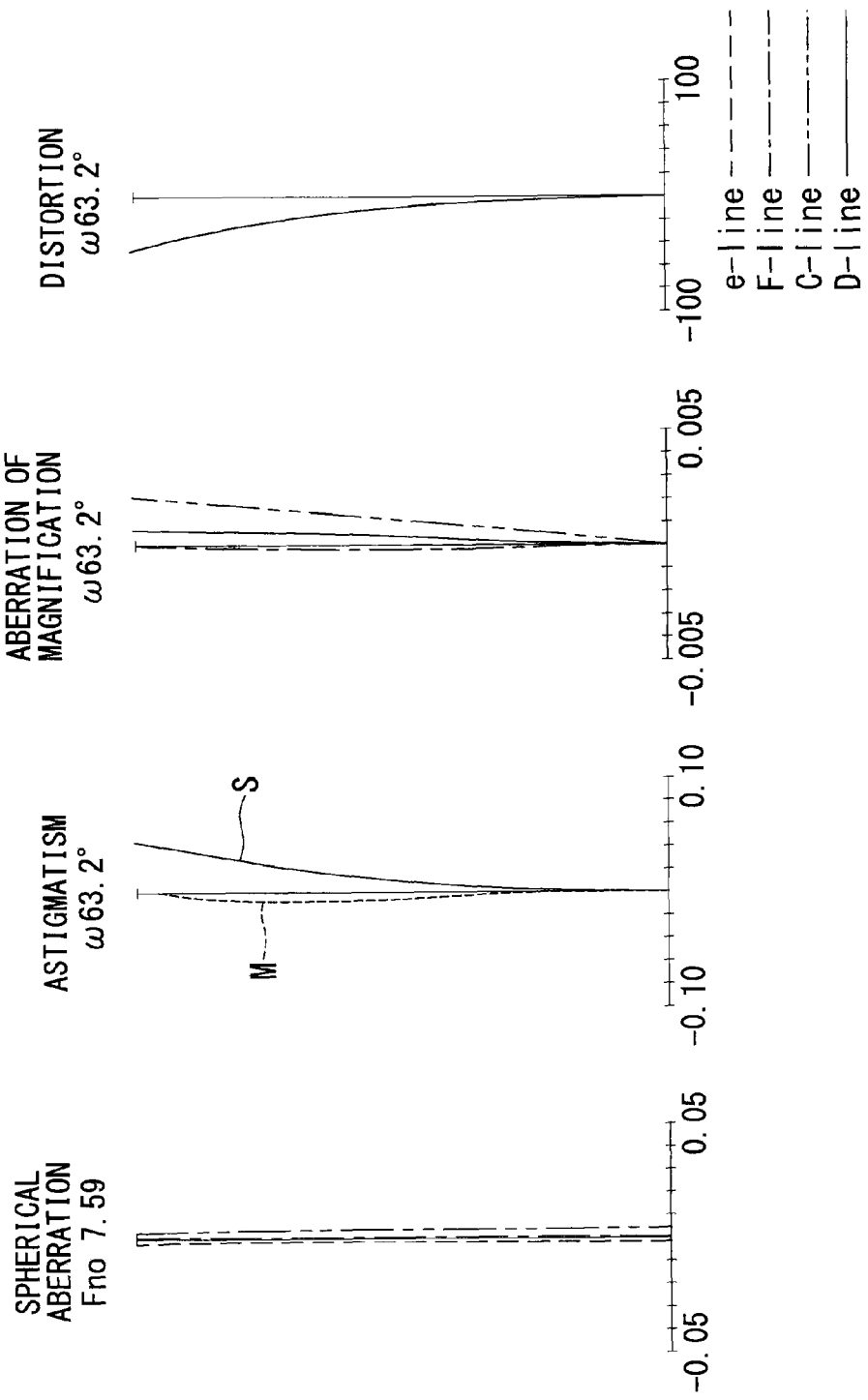
FIG. 5 shows aberration diagrams for the endoscope objective lens in the normal observation state shown in FIG. 3.
Figure 6:
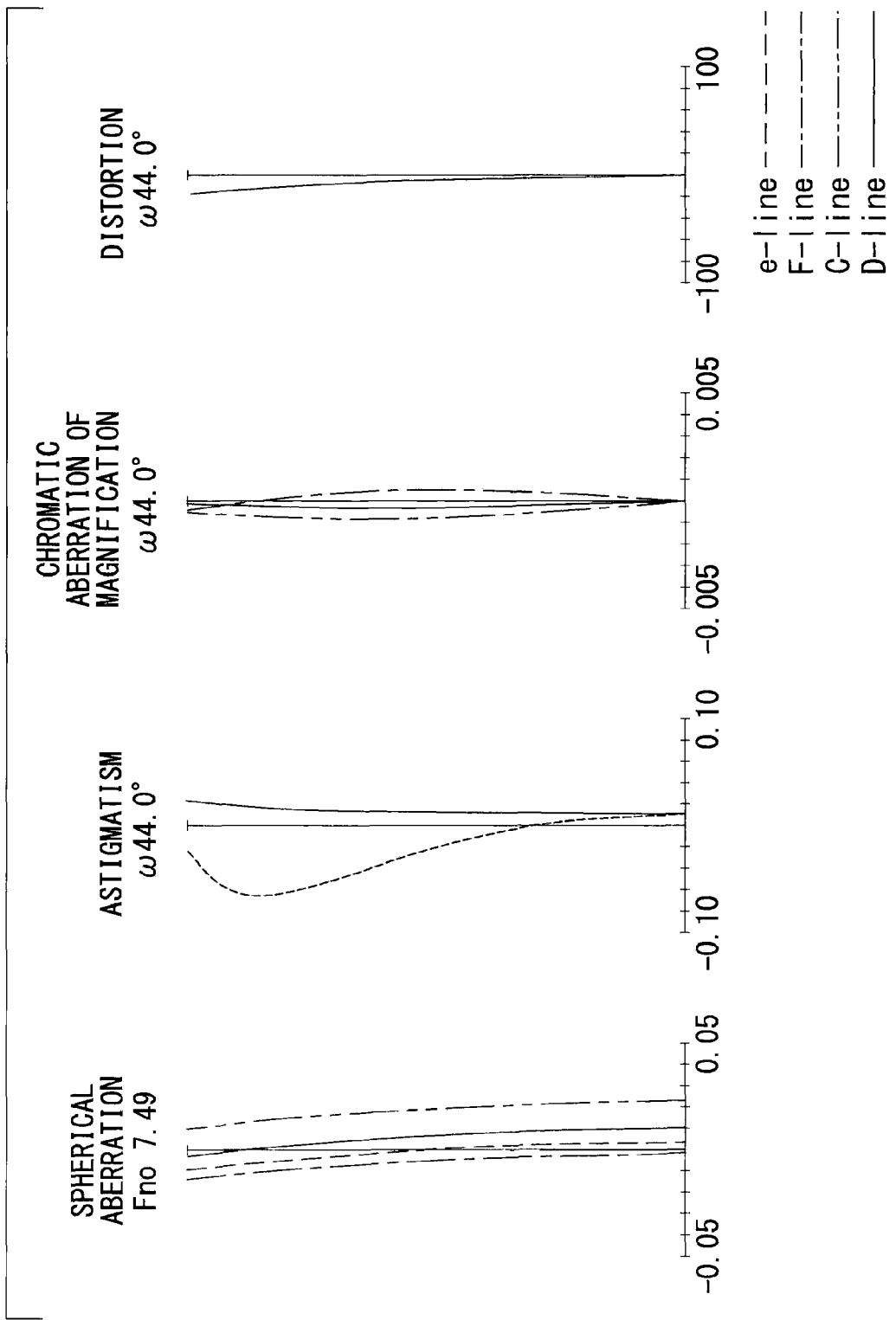
FIG. 6 shows aberration diagrams for the endoscope objective lens in the magnifying observation state shown in FIG. 4.

In FIGS. 3 and 4, $r_1$ to $r_9$ denote surfaces of the lenses constituting the positive first lens group 1, $r_{10}$ to $r_{12}$ denote surfaces of the lenses constituting the negative second lens group 2, and $r_{13}$ to $r_{22}$ denote surfaces of the lenses constituting the positive third lens group 3. The same applies to FIGS. 7, 8, 11, 12, 15, 16, 19, and 20. Furthermore, FIGS. 5 and 6 show spherical aberration, astigmatism, chromatic aberration of magnification, and distortion, corresponding to FIGS. 3 and 4, respectively. Furthermore, the endoscope objective lens 10 according to this example has the data shown in Tables 1, 2, and 3.

TABLE 1

| object surface | | $d_0$ | D0 | | | | |
|---|---|---|---|---|---|---|---|
| $r_1$ | ∞ | $d_1$ | 0.35 | $n_1$ | 1.88300 | $v_1$ | 40.76 |
| $r_2$ | 1.056 | $d_2$ | 0.70 | | | | |
| $r_3$ | ∞ | $d_3$ | 0.40 | $n_2$ | 1.52100 | $v_2$ | 65.13 |
| $r_4$ | ∞ | $d_4$ | 0.61 | | | | |
| $r_5$ | −1.967 | $d_5$ | 1.0 | $n_3$ | 1.58913 | $v_3$ | 61.14 |
| $r_6$ | −1.619 | $d_6$ | 0.05 | | | | |
| $r_7$ | 4.511 | $d_7$ | 1.30 | $n_4$ | 1.80100 | $v_4$ | 34.97 |
| $r_8$ | −2.191 | $d_8$ | 0.37 | $n_5$ | 1.92286 | $v_5$ | 18.9 |
| $r_9$ | −7.467 | $d_9$ | D9 | | | | |
| $r_{10}$ | ∞ | $d_{10}$ | 0.03 | | | | |
| $r_{11}$ | ∞ | $d_{11}$ | 0.30 | $n_6$ | 1.77250 | $v_6$ | 49.6 |
| $r_{12}$ | 1.240 | $d_{12}$ | 0.42 | $n_7$ | 1.59270 | $v_7$ | 35.31 |
| $r_{13}$ | ∞ | $d_{13}$ | D13 | | | | |
| $r_{14}$ | ∞ | $d_{14}$ | 1.43 | $n_8$ | 1.48749 | $v_8$ | 70.23 |
| $r_{15}$ | −2.297 | $d_{15}$ | 0.05 | | | | |
| $r_{16}$ | 4.815 | $d_{16}$ | 1.54 | $n_9$ | 1.48749 | $v_9$ | 70.23 |
| $r_{17}$ | −2.159 | $d_{17}$ | 0.45 | $n_{10}$ | 1.92286 | $v_{10}$ | 18.9 |
| $r_{18}$ | −6.198 | $d_{18}$ | 0.33 | | | | |
| $r_{19}$ | ∞ | $d_{19}$ | 0.40 | $n_{11}$ | 1.52300 | $v_{11}$ | 58.5 |
| $r_{20}$ | ∞ | $d_{20}$ | 0.68 | | | | |
| $r_{21}$ | ∞ | $d_{21}$ | 0.75 | $n_{12}$ | 1.51633 | $v_{12}$ | 64.14 |
| $r_{22}$ | ∞ | $d_{22}$ | 0.65 | $n_{13}$ | 1.50510 | $v_{13}$ | 63.26 |

TABLE 2

| | normal observation state | magnifying observation state |
|---|---|---|
| D0 | 14.5 | 2 |
| D9 | 0.2 | 1.8 |
| D13 | 1.9 | 0.3 |
| $f_1$ | 1.25 | 1.46 |
| $F_{no}$ | 7.59 | 7.49 |

TABLE 3

| Conditional Expressions (1)~(5) | |
|---|---|
| $f_2/f_W$ | −5.53 |
| $|f_M/f_W|$ | 5.94 |
| $f_3/f_2$ | −0.54 |
| $f_2/f_1$ | −3.25 |
| $f_3/f_1$ | 1.74 |

In the above-described data, data items corresponding to $r_1$ to $r_{22}$ are the radii of curvature of the surfaces of the lenses, data items corresponding to $d_1$ to $d_{22}$ are the thicknesses and intersurface distances of the lenses, data items corresponding to $n_1$ to $n_{13}$ are the refractive indexes of the lenses with respect to the d line, and data items corresponding to $v_1$ to $v_{13}$ are the Abbe numbers of the lenses with respect to the d line. Therefore, $d_0$ is the distance from the object surface to a first surface ($r_1$) of the objective lens. The unit of length represented by r and d is mm.

In this example, because the endoscope objective lens 10 satisfies Conditional Expressions (1) to (5), manufacturing errors are suppressed, and the aberrations are successfully removed.

Reference Example 1

Figure 7:
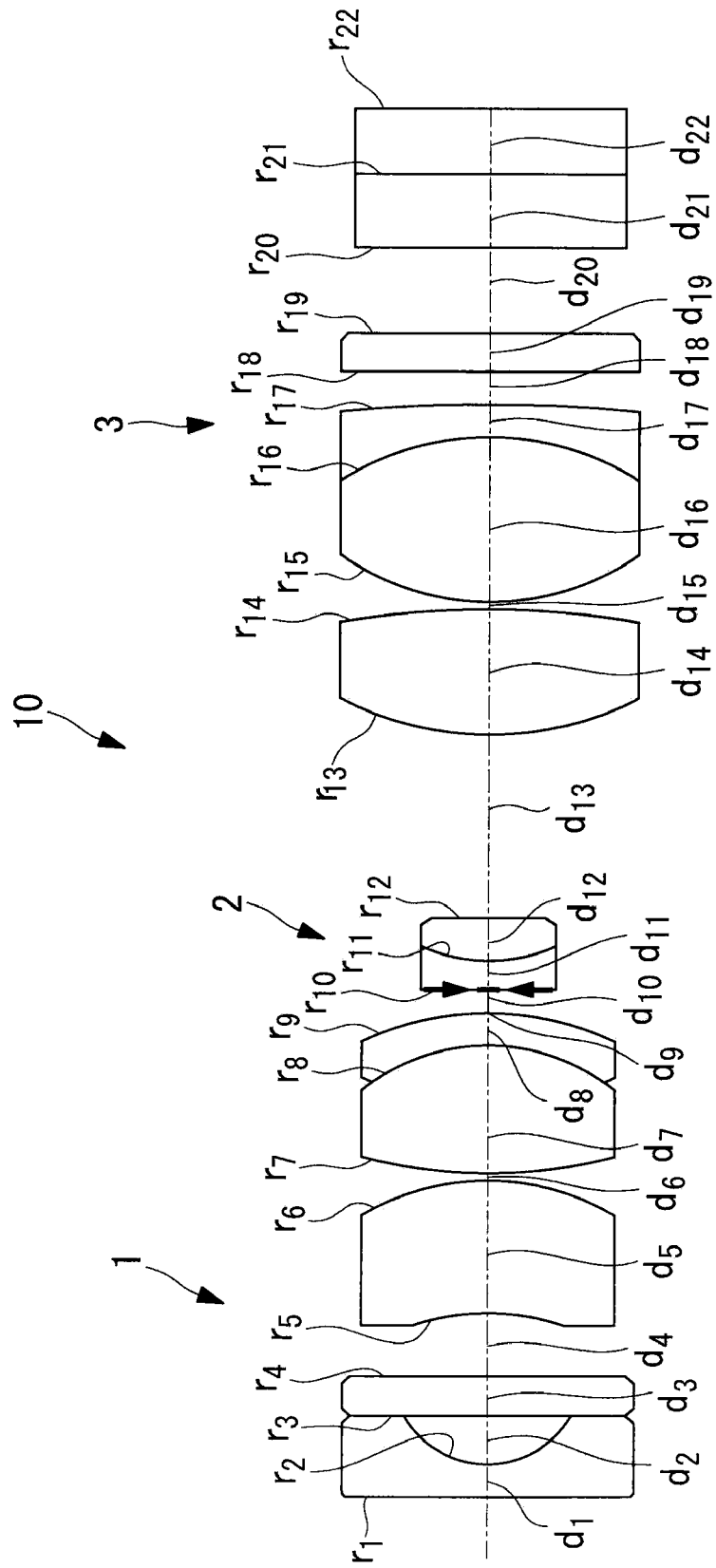
FIG. 7 is a view showing the normal observation state of an endoscope objective lens according to Reference Example 1 of the invention, as a reference example of the present invention.
Figure 8:
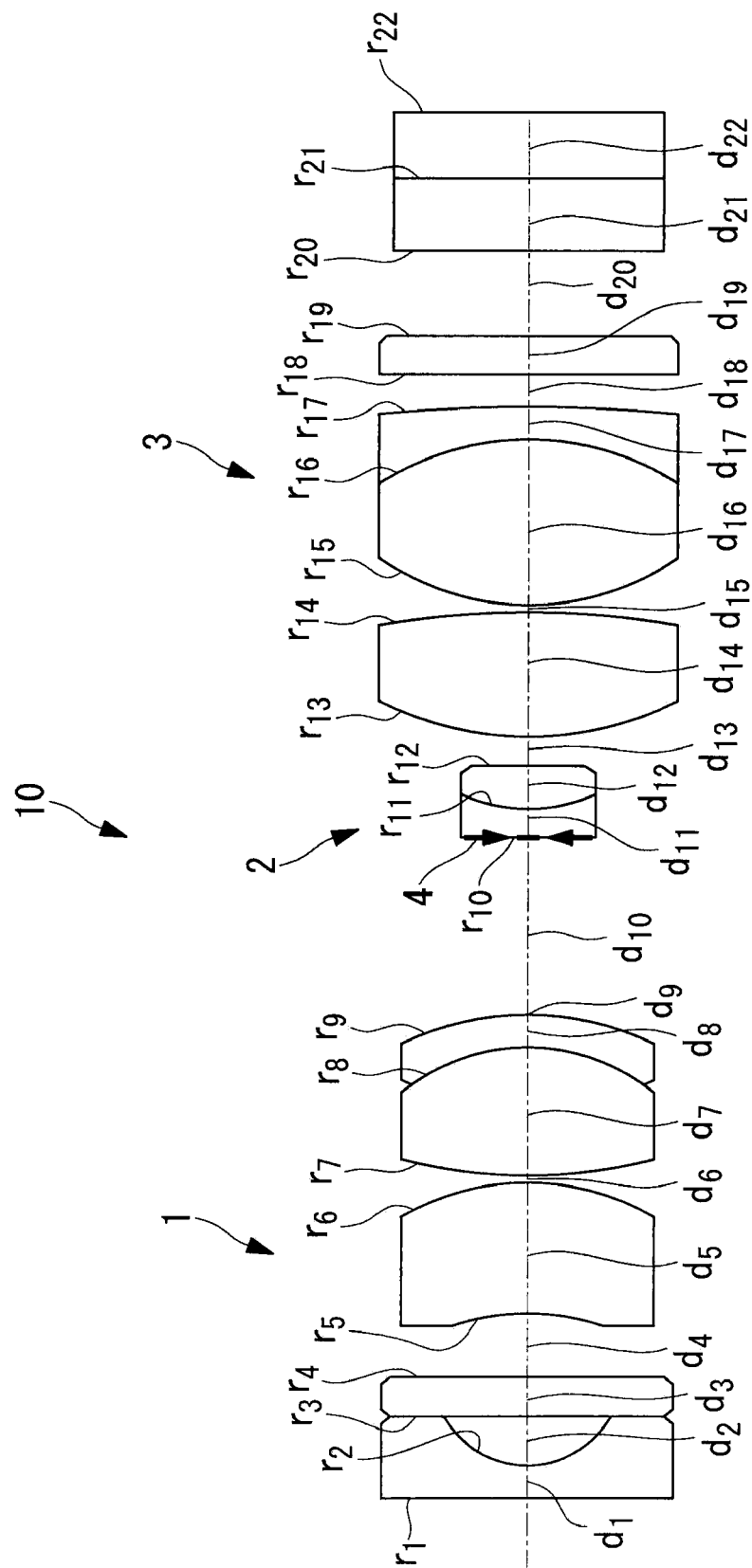
FIG. 8 is a view showing the magnifying observation state of the endoscope objective lens according to Reference Example 1 of the invention, as a reference example of the present invention.
Figure 9:
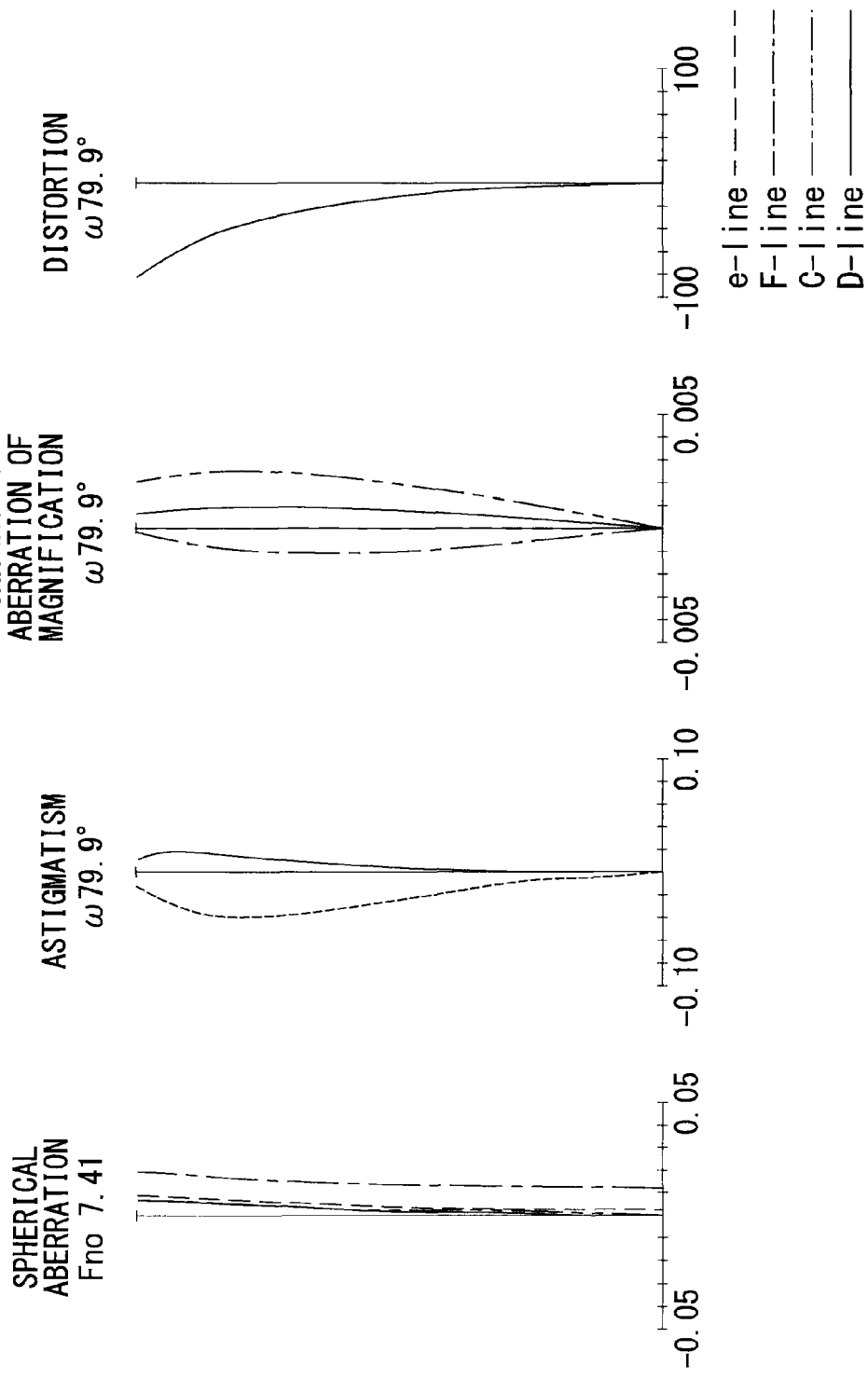
FIG. 9 shows aberration diagrams for the endoscope objective lens in the normal observation state shown in FIG. 7.
Figure 10:
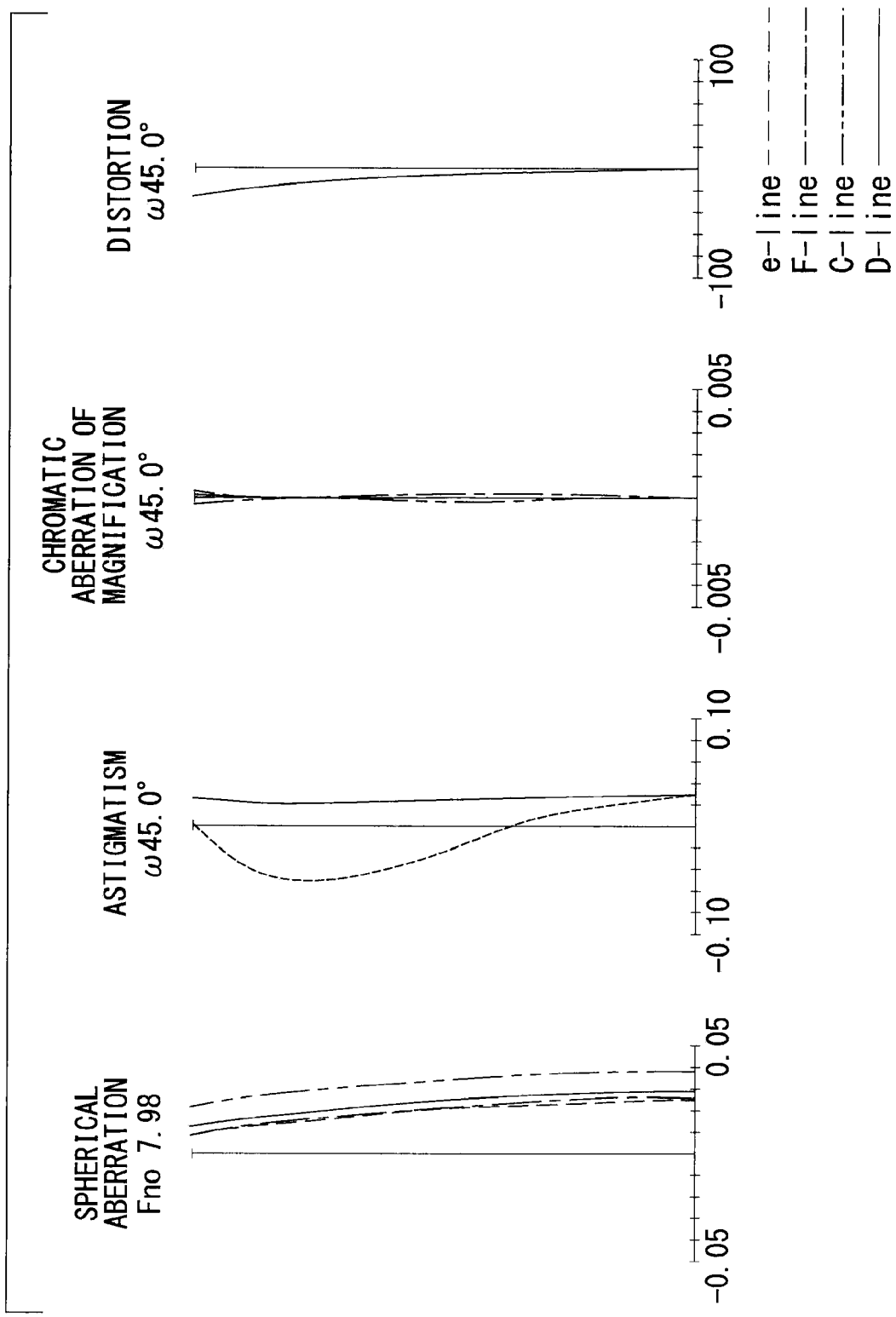
FIG. 10 shows aberration diagrams for the endoscope objective lens in the magnifying observation state shown in FIG. 8.

An endoscope objective lens 10 according to Reference Example 1 of the invention, as a reference example of the present invention, is shown in FIGS. 7 and 8. FIG. 7 shows the normal observation state, in which the second lens group 2 has been moved toward the object. FIG. 8 shows the magnifying observation state, in which the second lens group 2 has been moved toward the image. Furthermore, FIGS. 9 and 10 show spherical aberration, astigmatism, chromatic aberration of magnification, and distortion, corresponding to FIGS. 7 and 8, respectively. Furthermore, the endoscope objective lens 10 according to this example has the data shown in Tables 4, 5, and 6.

TABLE 4

| object surface | | $d_0$ | D0 | | | | |
|---|---|---|---|---|---|---|---|
| $r_1$ | ∞ | $d_1$ | 0.35 | $n_1$ | 1.88300 | $v_1$ | 40.76 |
| $r_2$ | 1.051 | $d_2$ | 0.48 | | | | |
| $r_3$ | ∞ | $d_3$ | 0.40 | $n_2$ | 1.52100 | $v_2$ | 65.13 |
| $r_4$ | ∞ | $d_4$ | 0.60 | | | | |
| $r_5$ | −3.073 | $d_5$ | 1.30 | $n_3$ | 1.69680 | $v_3$ | 55.53 |
| $r_6$ | −3.020 | $d_6$ | 0.05 | | | | |
| $r_7$ | 6.393 | $d_7$ | 1.23 | $n_4$ | 1.77250 | $v_4$ | 49.6 |
| $r_8$ | −2.178 | $d_8$ | 0.34 | $n_5$ | 1.92286 | $v_5$ | 18.9 |
| $r_9$ | −3.445 | $d_9$ | D9 | | | | |
| $r_{10}$ | ∞ | $d_{10}$ | 0.03 | | | | |
| $r_{11}$ | ∞ | $d_{11}$ | 0.30 | $n_6$ | 1.77250 | $v_6$ | 49.6 |
| $r_{12}$ | 1.542 | $d_{12}$ | 0.42 | $n_7$ | 1.59270 | $v_7$ | 35.31 |
| $r_{13}$ | 8.817 | $d_{13}$ | D13 | | | | |
| $r_{14}$ | 3.549 | $d_{14}$ | 1.23 | $n_8$ | 1.48749 | $v_8$ | 70.23 |
| $r_{15}$ | −9.319 | $d_{15}$ | 0.05 | | | | |
| $r_{16}$ | 2.879 | $d_{16}$ | 1.61 | $n_9$ | 1.48749 | $v_9$ | 70.23 |
| $r_{17}$ | −2.799 | $d_{17}$ | 0.33 | $n_{10}$ | 1.92286 | $v_{10}$ | 18.9 |
| $r_{18}$ | −15.968 | $d_{18}$ | 0.33 | | | | |
| $r_{19}$ | ∞ | $d_{19}$ | 0.40 | $n_{11}$ | 1.52300 | $v_{11}$ | 58.5 |
| $r_{20}$ | ∞ | $d_{20}$ | 0.81 | | | | |
| $r_{21}$ | ∞ | $d_{21}$ | 0.75 | $n_{12}$ | 1.51633 | $v_{12}$ | 64.14 |
| $r_{22}$ | ∞ | $d_{22}$ | 0.65 | $n_{13}$ | 1.50510 | $v_{13}$ | 63.26 |

TABLE 5

| | normal observation state | magnifying observation state |
|---|---|---|
| D0 | 12 | 2 |
| D9 | 0.2 | 1.8 |
| D13 | 1.9 | 0.3 |
| $f_1$ | 1.19 | 1.44 |
| $F_{no}$ | 7.41 | 7.98 |

TABLE 6

| Conditional Expressions (1)~(5) | |
|---|---|
| $f_2/f_W$ | −4.51 |
| $|f_M/f_W|$ | 19.0 |
| $f_3/f_2$ | −0.67 |
| $f_2/f_1$ | −2.53 |
| $f_3/f_1$ | 1.69 |

In this example, because the endoscope objective lens 10 satisfies Conditional Expressions (1) to (5), manufacturing errors are suppressed, and the aberrations are successfully removed.

Example 2 of Present Invention

Figure 11:
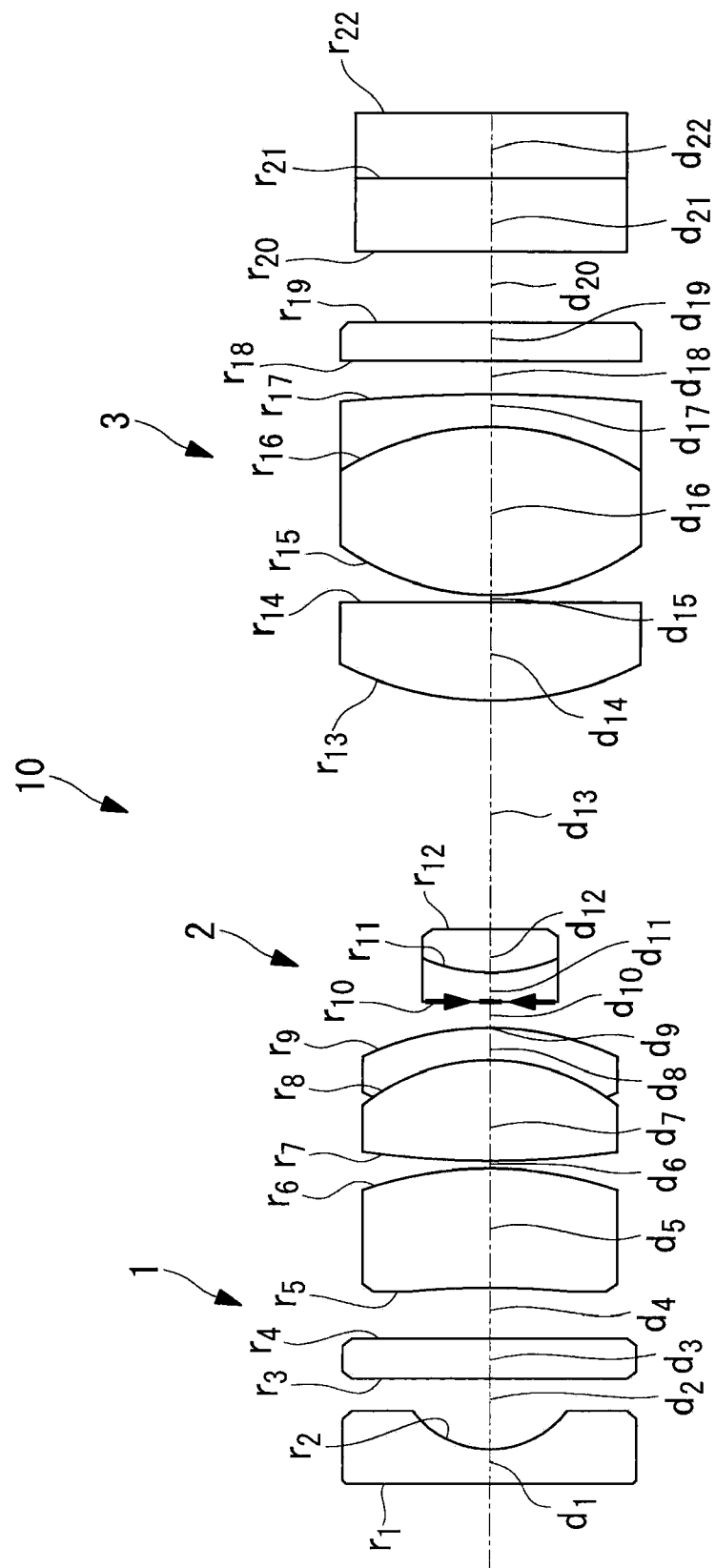
FIG. 11 is a view showing the normal observation state of an endoscope objective lens according to Example 2 of the embodiment of the present invention.
Figure 12:
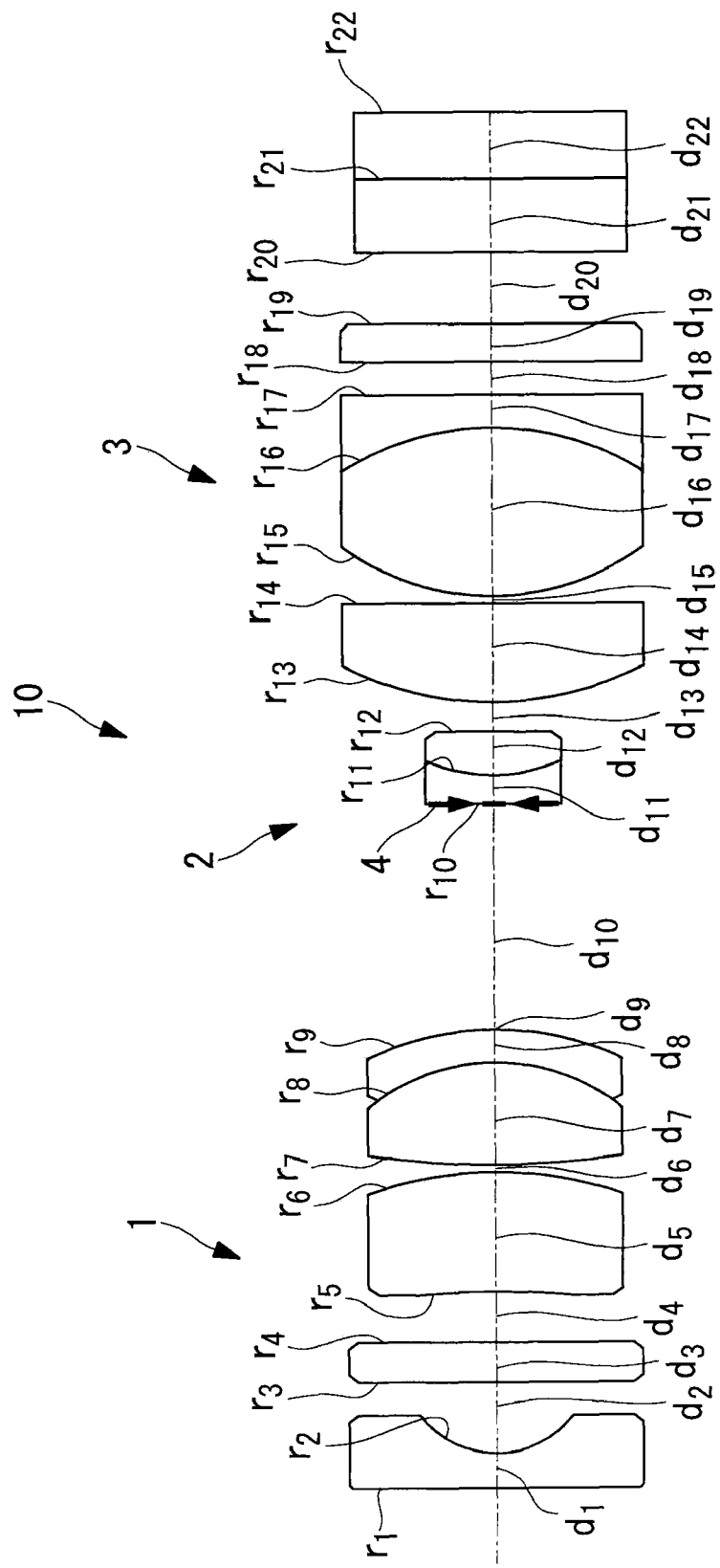
FIG. 12 is a view showing the magnifying observation state of the endoscope objective lens according to Example 2 of the embodiment of the present invention.
Figure 13:
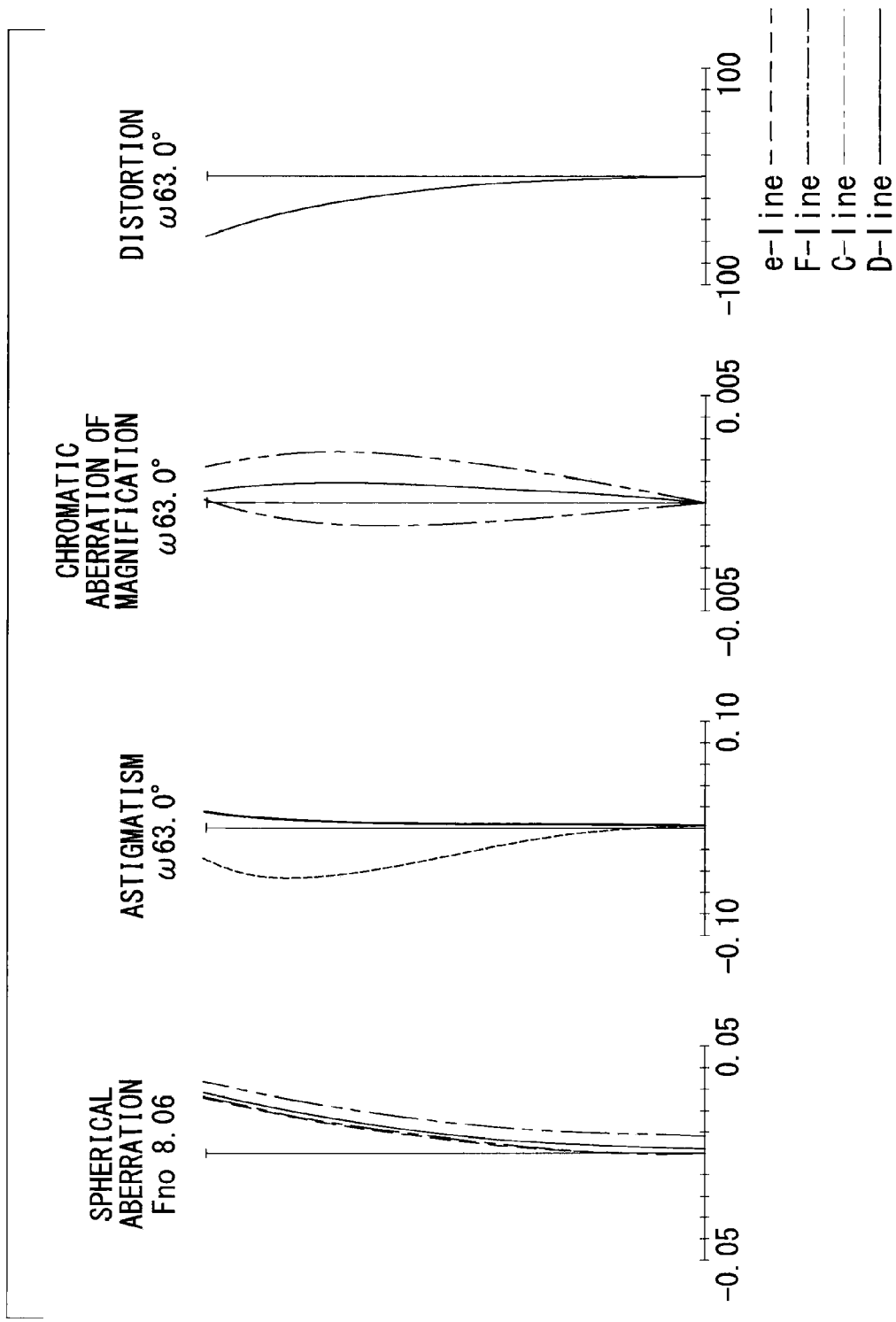
FIG. 13 shows aberration diagrams for the endoscope objective lens in the normal observation state shown in FIG. 11.
Figure 14:
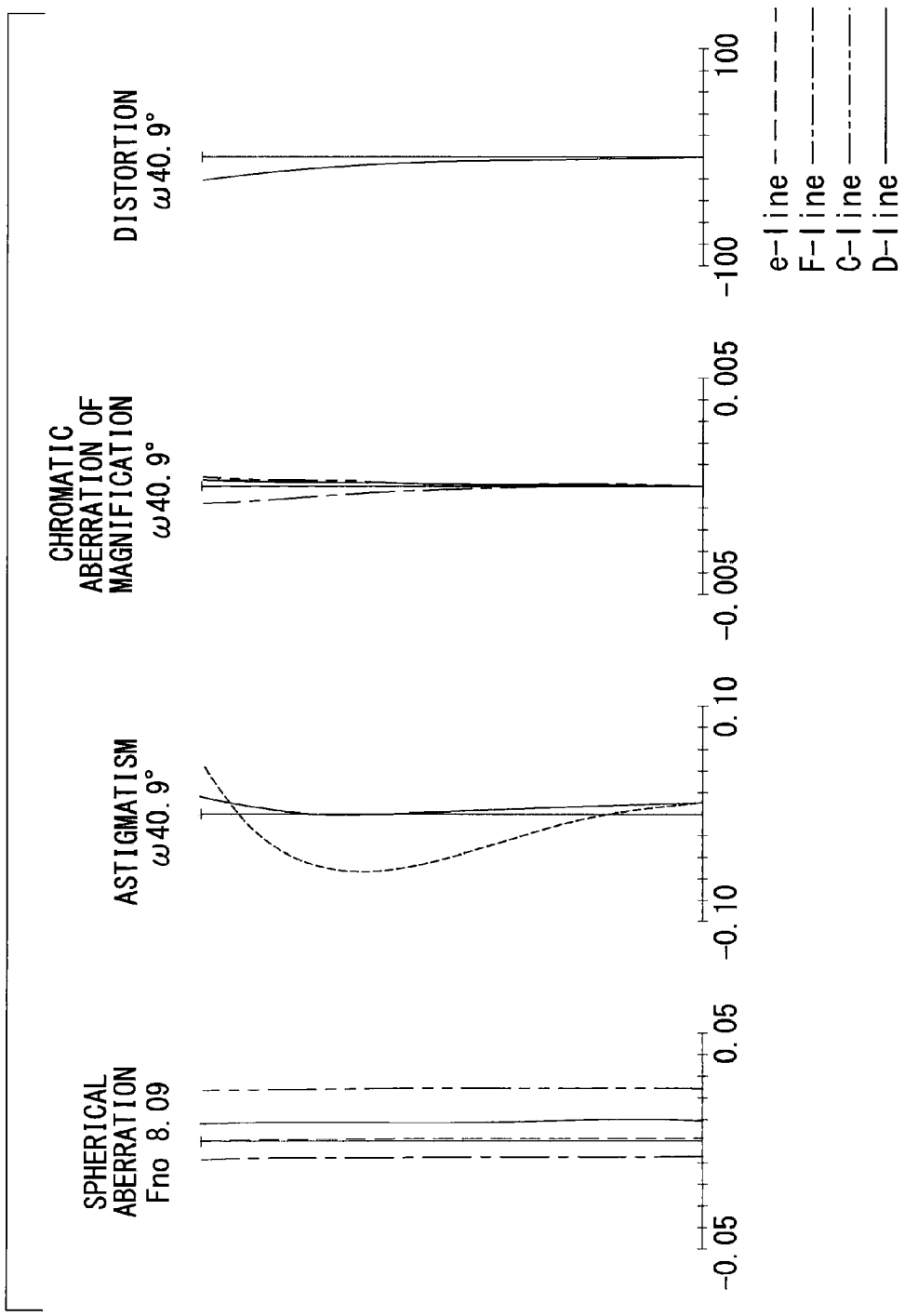
FIG. 14 shows aberration diagrams for the endoscope objective lens in the magnifying observation state shown in FIG. 12.

An endoscope objective lens 10 according to Example 2 of the present invention is shown in FIGS. 11 and 12. FIG. 11 shows the normal observation state, in which the second lens group 2 has been moved toward the object. FIG. 12 shows the magnifying observation state, in which the second lens group 2 has been moved toward the image. Furthermore, FIGS. 13 and 14 show spherical aberration, astigmatism, chromatic aberration of magnification, and distortion, corresponding to FIGS. 11 and 12, respectively. Furthermore, the endoscope objective lens 10 according to this example has the data shown in Tables 7, 8, and 9.

TABLE 7

| object surface | | $d_0$ | D0 | | | | |
|---|---|---|---|---|---|---|---|
| $r_1$ | ∞ | $d_1$ | 0.35 | $n_1$ | 1.88300 | $v_1$ | 40.76 |
| $r_2$ | 1.052 | $d_2$ | 0.71 | | | | |
| $r_3$ | ∞ | $d_3$ | 0.40 | $n_2$ | 1.52100 | $v_2$ | 65.13 |
| $r_4$ | ∞ | $d_4$ | 0.50 | | | | |
| $r_5$ | −9.095 | $d_5$ | 1.20 | $n_3$ | 1.69680 | $v_3$ | 55.53 |
| $r_6$ | −4.411 | $d_6$ | 0.05 | | | | |
| $r_7$ | 10.770 | $d_7$ | 1.00 | $n_4$ | 1.77250 | $v_4$ | 49.6 |
| $r_8$ | −1.970 | $d_8$ | 0.34 | $n_5$ | 1.92286 | $v_5$ | 18.9 |
| $r_9$ | −3.048 | $d_9$ | D9 | | | | |
| $r_{10}$ | ∞ | $d_{10}$ | 0.03 | | | | |
| $r_{11}$ | ∞ | $d_{11}$ | 0.30 | $n_6$ | 1.77250 | $v_6$ | 49.6 |
| $r_{12}$ | 1.389 | $d_{12}$ | 0.42 | $n_7$ | 1.59270 | $v_7$ | 35.31 |
| $r_{13}$ | ∞ | $d_{13}$ | D13 | | | | |
| $r_{14}$ | 3.517 | $d_{14}$ | 1.00 | $n_8$ | 1.48749 | $v_8$ | 70.23 |
| $r_{15}$ | −63.204 | $d_{15}$ | 0.05 | | | | |
| $r_{16}$ | 2.611 | $d_{16}$ | 1.63 | $n_9$ | 1.48749 | $v_9$ | 70.23 |
| $r_{17}$ | −3.191 | $d_{17}$ | 0.33 | $n_{10}$ | 1.92286 | $v_{10}$ | 18.9 |
| $r_{18}$ | ∞ | $d_{18}$ | 0.33 | | | | |
| $r_{19}$ | ∞ | $d_{19}$ | 0.40 | $n_{11}$ | 1.52300 | $v_{11}$ | 58.5 |
| $r_{20}$ | ∞ | $d_{20}$ | 0.70 | | | | |
| $r_{21}$ | ∞ | $d_{21}$ | 0.75 | $n_{12}$ | 1.51633 | $v_{12}$ | 64.14 |
| $r_{22}$ | ∞ | $d_{22}$ | 0.65 | $n_{13}$ | 1.50510 | $v_{13}$ | 63.26 |

TABLE 8

| | normal observation state | magnifying observation state |
|---|---|---|
| D0 | 12 | 2 |
| D9 | 0.2 | 2.2 |
| D13 | 2.3 | 0.3 |
| $f_1$ | 1.34 | 1.52 |
| $F_{no}$ | 8.06 | 8.09 |

TABLE 9

| Conditional Expressions (1)~(5) | |
|---|---|
| $f_2/f_W$ | −5.78 |
| $|f_M/f_W|$ | 8.3 |
| $f_3/f_2$ | −0.54 |
| $f_2/f_1$ | −3.24 |
| $f_3/f_1$ | 1.77 |

In this example, because the endoscope objective lens 10 satisfies Conditional Expressions (1) to (5), manufacturing errors are suppressed, and the aberrations are successfully removed.

Reference Example 2

Figure 15:
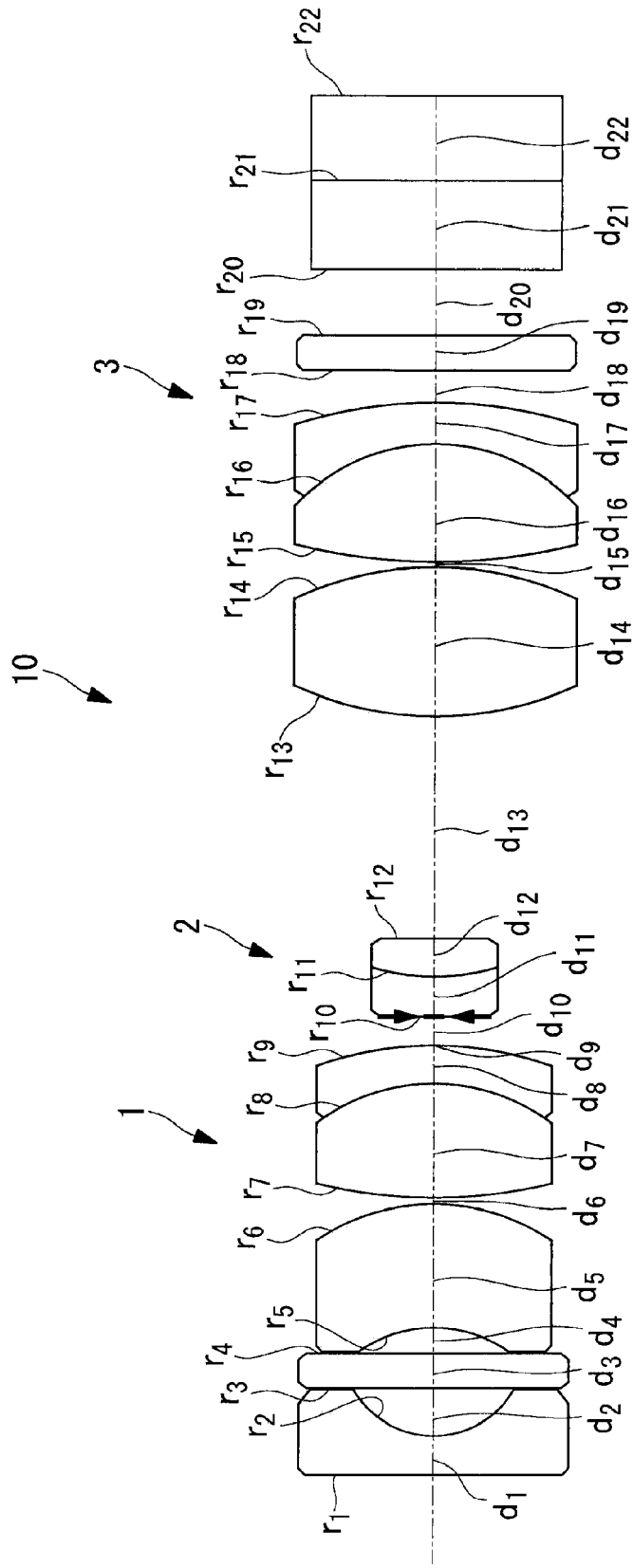
FIG. 15 is a view showing the normal observation state of an endoscope objective lens according to Reference Example 2 of the invention, as a reference example of the present invention.
Figure 16:
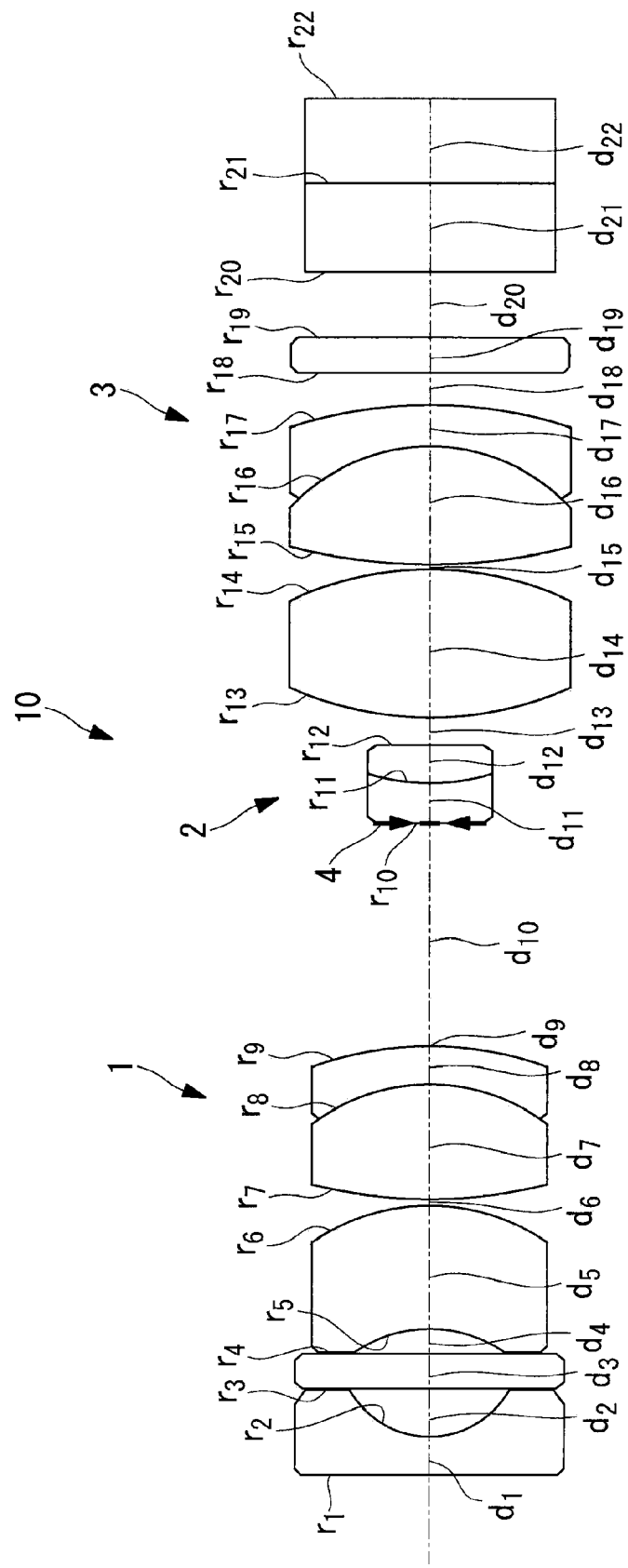
FIG. 16 is a view showing the magnifying observation state of the endoscope objective lens according to Reference Example 2 of the invention, as a reference example of the present invention.
Figure 17:
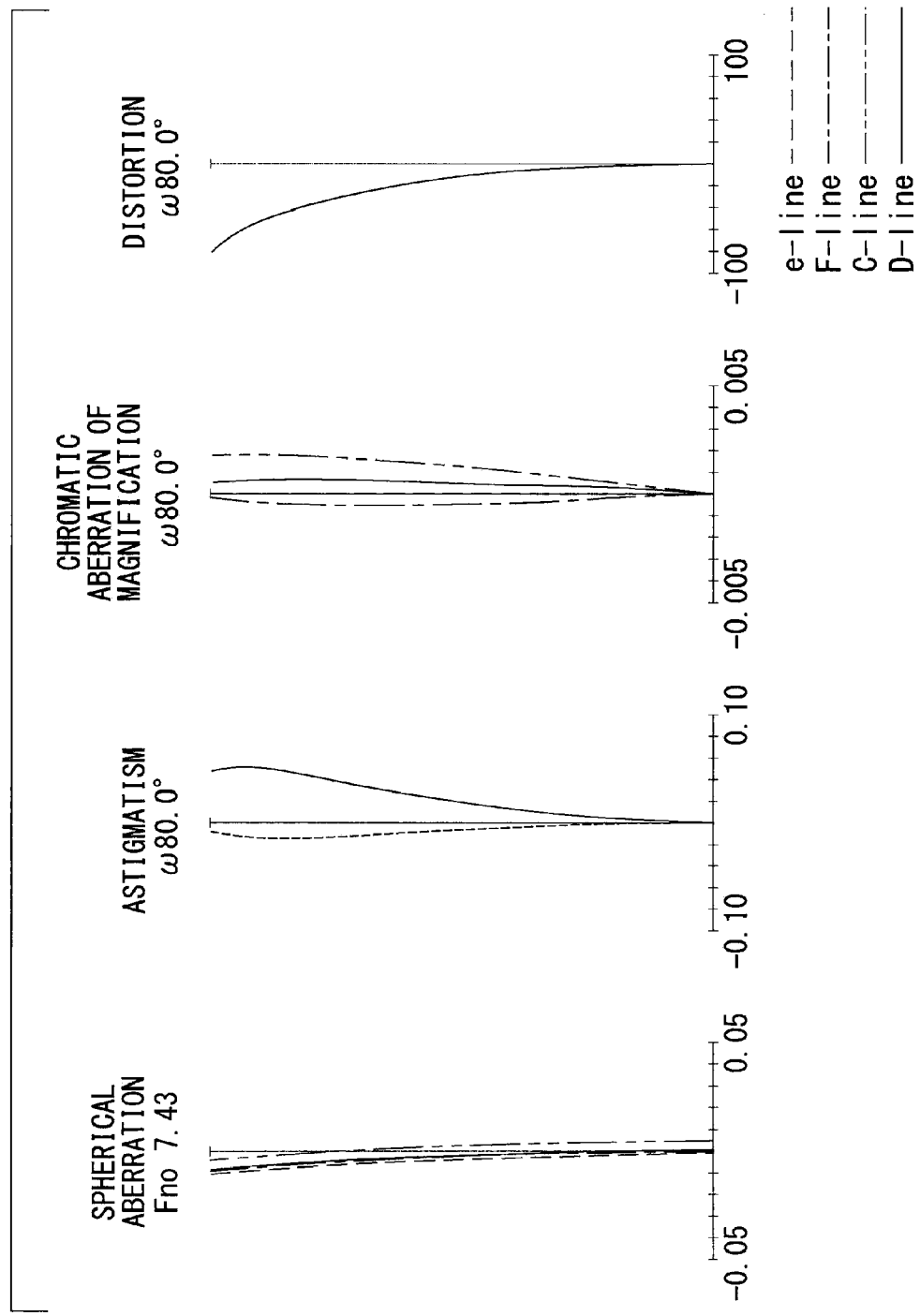
FIG. 17 shows aberration diagrams for the endoscope objective lens in the normal observation state shown in FIG. 15.
Figure 18:
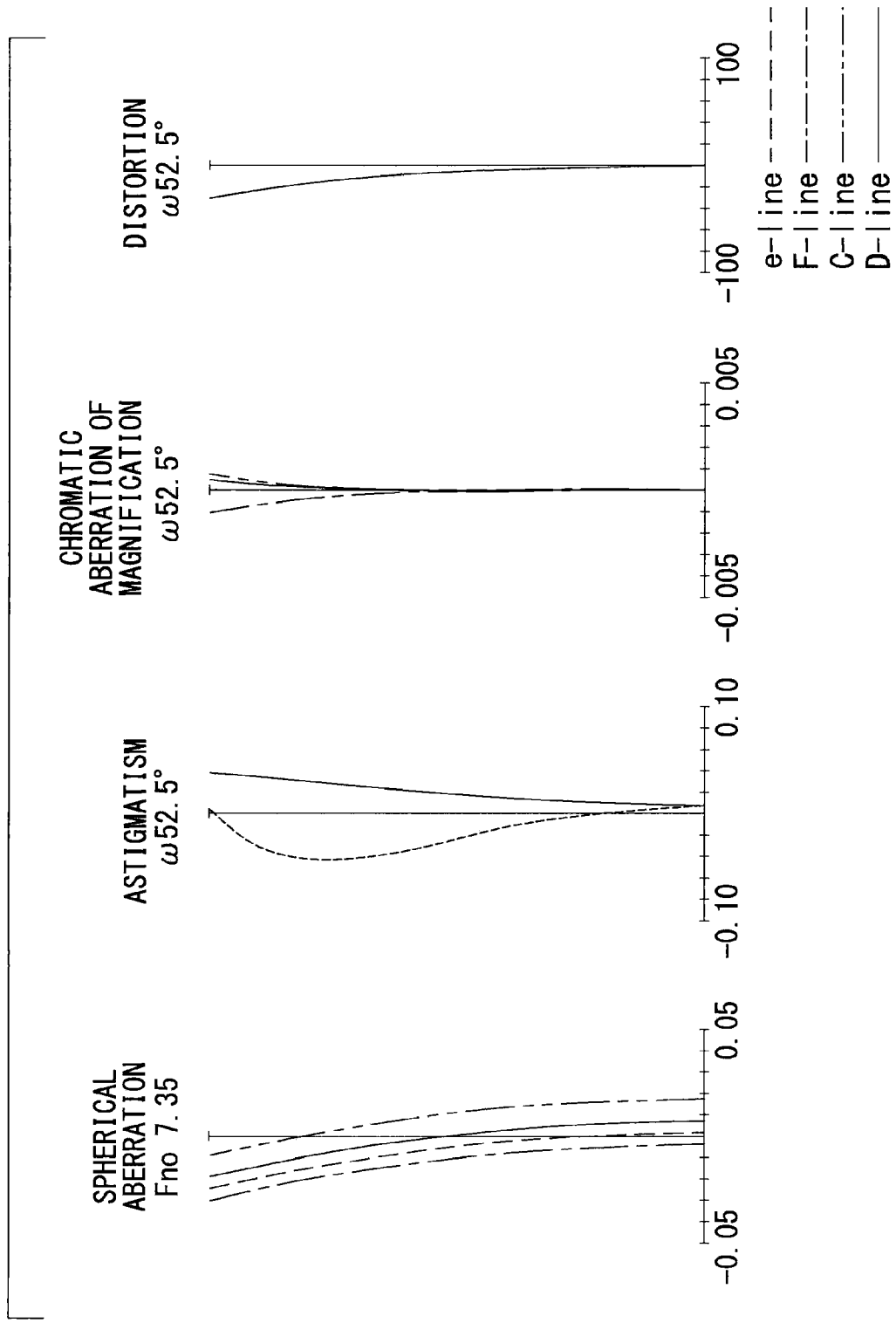
FIG. 18 shows aberration diagrams for the endoscope objective lens in the magnifying observation state shown in FIG. 16.

An endoscope objective lens 10 according to Reference Example 2 of the invention, as a reference example of the present invention, is shown in FIGS. 15 and 16. FIG. 15 shows the normal observation state, in which the second lens group 2 has been moved toward the object. FIG. 16 shows the magnifying observation state, in which the second lens group 2 has been moved toward the image. Furthermore, FIGS. 17 and 18 show spherical aberration, astigmatism, chromatic aberration of magnification, and distortion, corresponding to FIGS. 15 and 16, respectively. Furthermore, the endoscope objective lens 10 according to this example has the data shown in Tables 10, 11, and 12.

TABLE 10

| object surface | | $d_0$ | D0 | | | | |
|---|---|---|---|---|---|---|---|
| $r_1$ | ∞ | $d_1$ | 0.32 | $n_1$ | 1.88300 | $v_1$ | 40.76 |
| $r_2$ | 0.747 | $d_2$ | 0.37 | | | | |
| $r_3$ | ∞ | $d_3$ | 0.30 | $n_2$ | 1.52100 | $v_2$ | 65.13 |
| $r_4$ | ∞ | $d_4$ | 0.20 | | | | |
| $r_5$ | −1.107 | $d_5$ | 1.01 | $n_3$ | .69895 | $v_3$ | 30.13 |
| $r_6$ | −1.681 | $d_6$ | 0.03 | | | | |
| $r_7$ | 5.058 | $d_7$ | 0.94 | $n_4$ | 1.77250 | $v_4$ | 49.6 |
| $r_8$ | −1.572 | $d_8$ | 0.32 | $n_5$ | 1.92286 | $v_5$ | 18.9 |
| $r_9$ | −2.576 | $d_9$ | D9 | | | | |
| $r_{10}$ | ∞ | $d_{10}$ | 0.03 | | | | |
| $r_{11}$ | ∞ | $d_{11}$ | 0.30 | $n_6$ | 1.77250 | $v_6$ | 49.6 |
| $r_{12}$ | 1.409 | $d_{12}$ | 0.32 | $n_7$ | 1.59270 | $v_7$ | 35.31 |
| $r_{13}$ | ∞ | $d_{13}$ | D13 | | | | |
| $r_{14}$ | 3.089 | $d_{14}$ | 1.20 | $n_8$ | 1.48749 | $v_8$ | 70.23 |
| $r_{15}$ | −3.001 | $d_{15}$ | 0.05 | | | | |
| $r_{16}$ | 10.794 | $d_{16}$ | 0.94 | $n_9$ | 1.48749 | $v_9$ | 70.23 |
| $r_{17}$ | −1.670 | $d_{17}$ | 0.34 | $n_{10}$ | 1.92286 | $v_{10}$ | 18.9 |
| $r_{18}$ | −4.015 | $d_{18}$ | 0.25 | | | | |
| $r_{19}$ | ∞ | $d_{19}$ | 0.30 | $n_{11}$ | 1.52100 | $v_{11}$ | 65.13 |
| $r_{20}$ | ∞ | $d_{20}$ | 0.53 | | | | |
| $r_{21}$ | ∞ | $d_{21}$ | 0.70 | $n_{12}$ | 1.51633 | $v_{12}$ | 64.14 |
| $r_{22}$ | ∞ | $d_{22}$ | 0.70 | $n_{13}$ | 1.50510 | $v_{13}$ | 63.26 |

TABLE 11

| | normal observation state | magnifying observation state |
|---|---|---|
| D0 | 7.5 | 1.6 |
| D9 | 0.2 | 1.8. |
| D13 | 1.8 | 0.2 |
| $f_1$ | 0.89 | 1.03 |
| $F_{no}$ | 7.43 | 7.35 |

TABLE 12

| Conditional Expressions (1)~(5) | |
|---|---|
| $f_2/f_W$ | −8.79 |
| $|f_M/f_W|$ | 19.0 |
| $f_3/f_2$ | −0.41 |
| $f_2/f_1$ | −4.03 |
| $f_3/f_1$ | 1.65 |

In this example, because the endoscope objective lens 10 satisfies Conditional Expressions (1) to (5), manufacturing errors are suppressed, and the aberrations are successfully removed.

Reference Example 3

Figure 19:
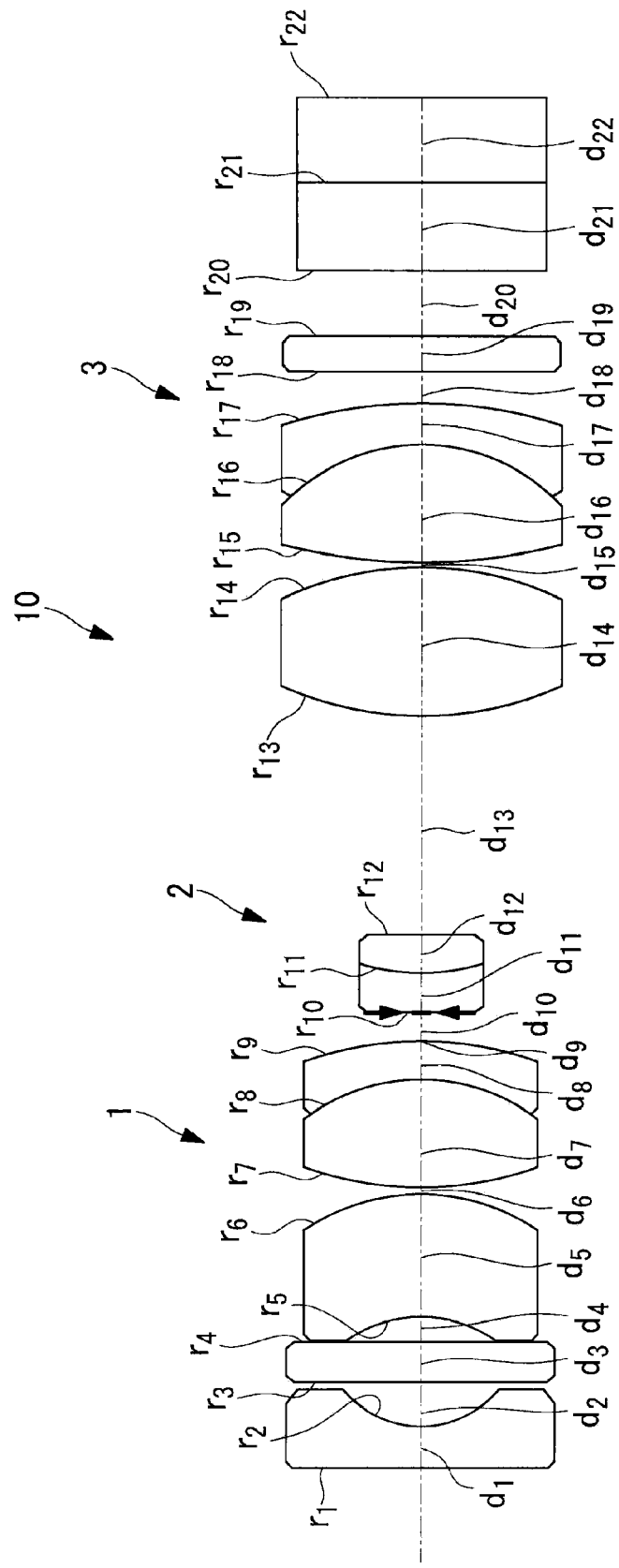
FIG. 19 is a view showing the normal observation state of an endoscope objective lens according to Reference Example 3 of the invention, as a reference example of the present invention.
Figure 20:
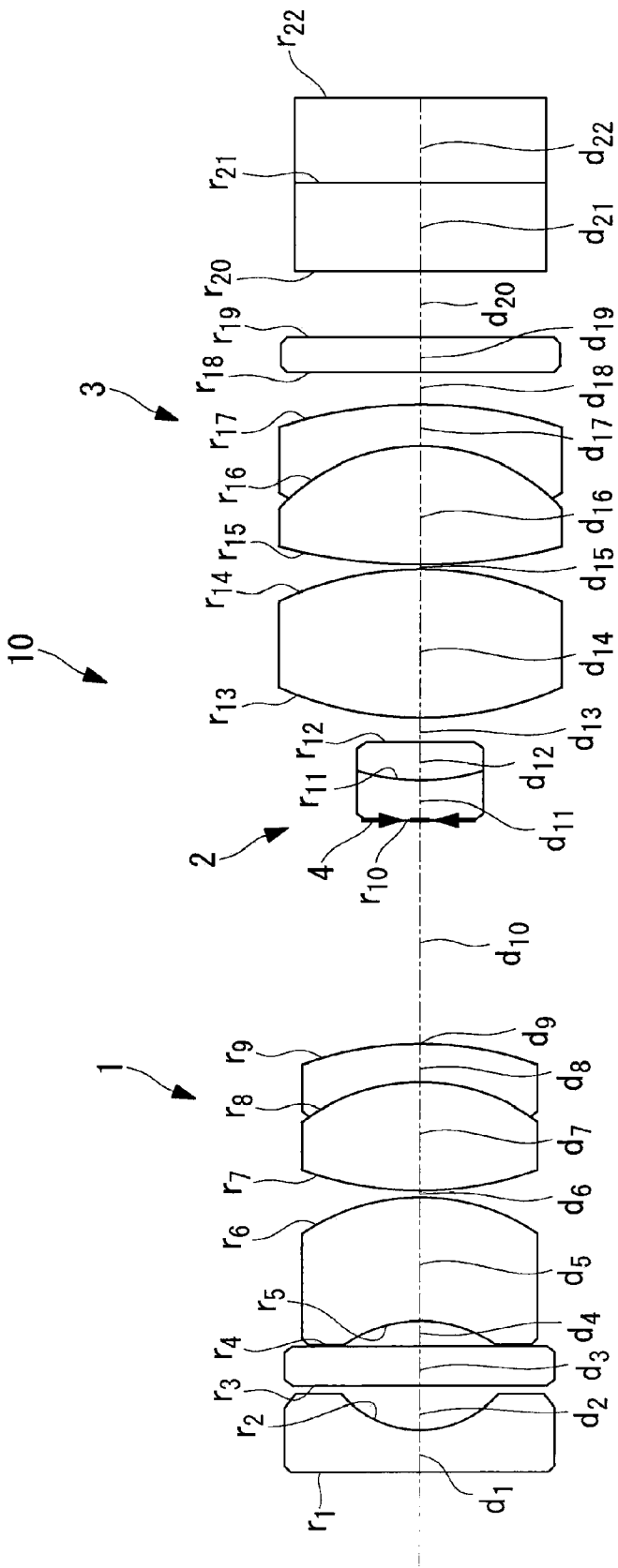
FIG. 20 is a view showing the magnifying observation state of the endoscope objective lens according to Reference Example 3 of the invention, as a reference example of the present invention.
Figure 21:
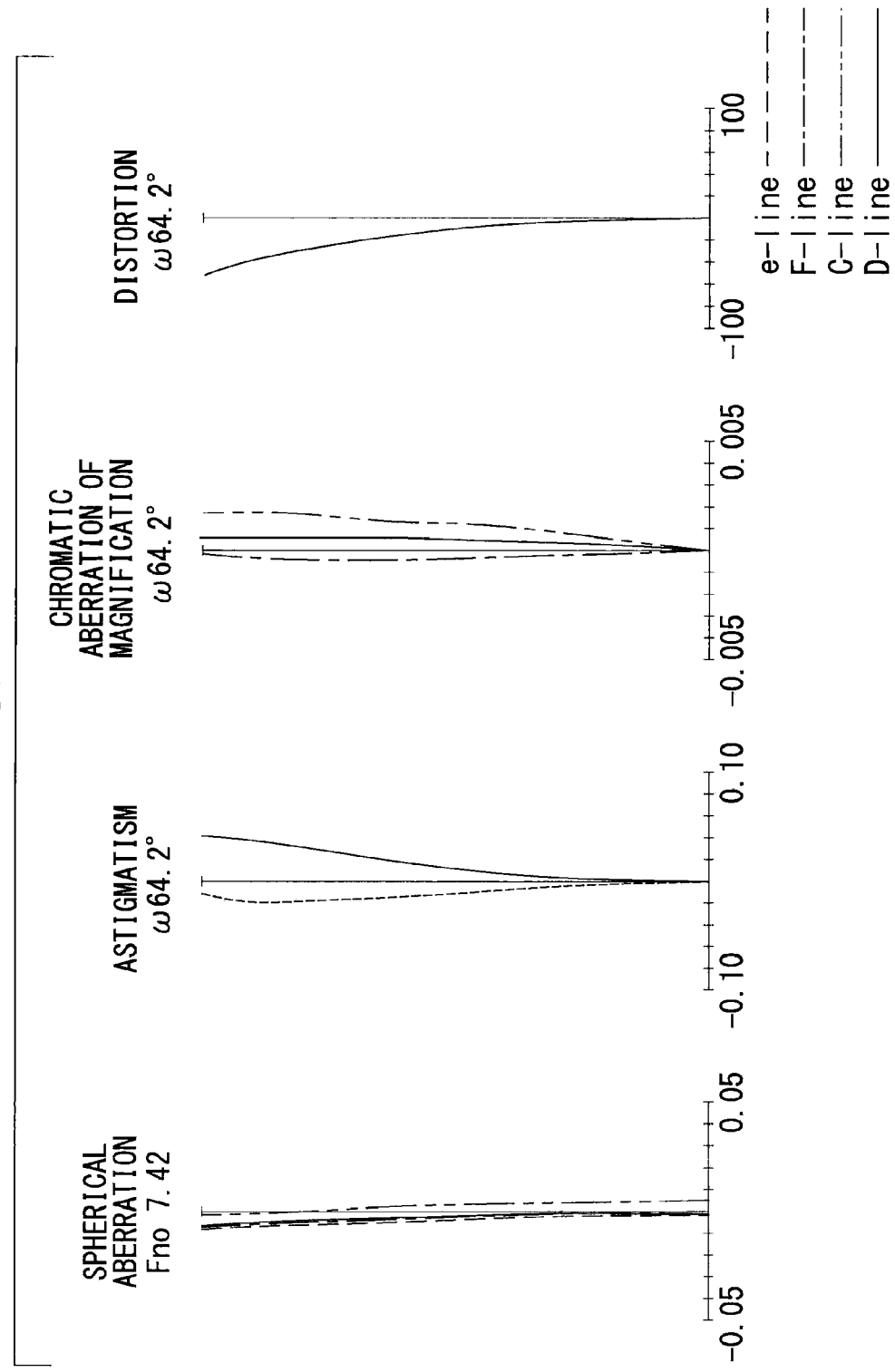
FIG. 21 shows aberration diagrams for the endoscope objective lens in the normal observation state shown in FIG. 19.
Figure 22:
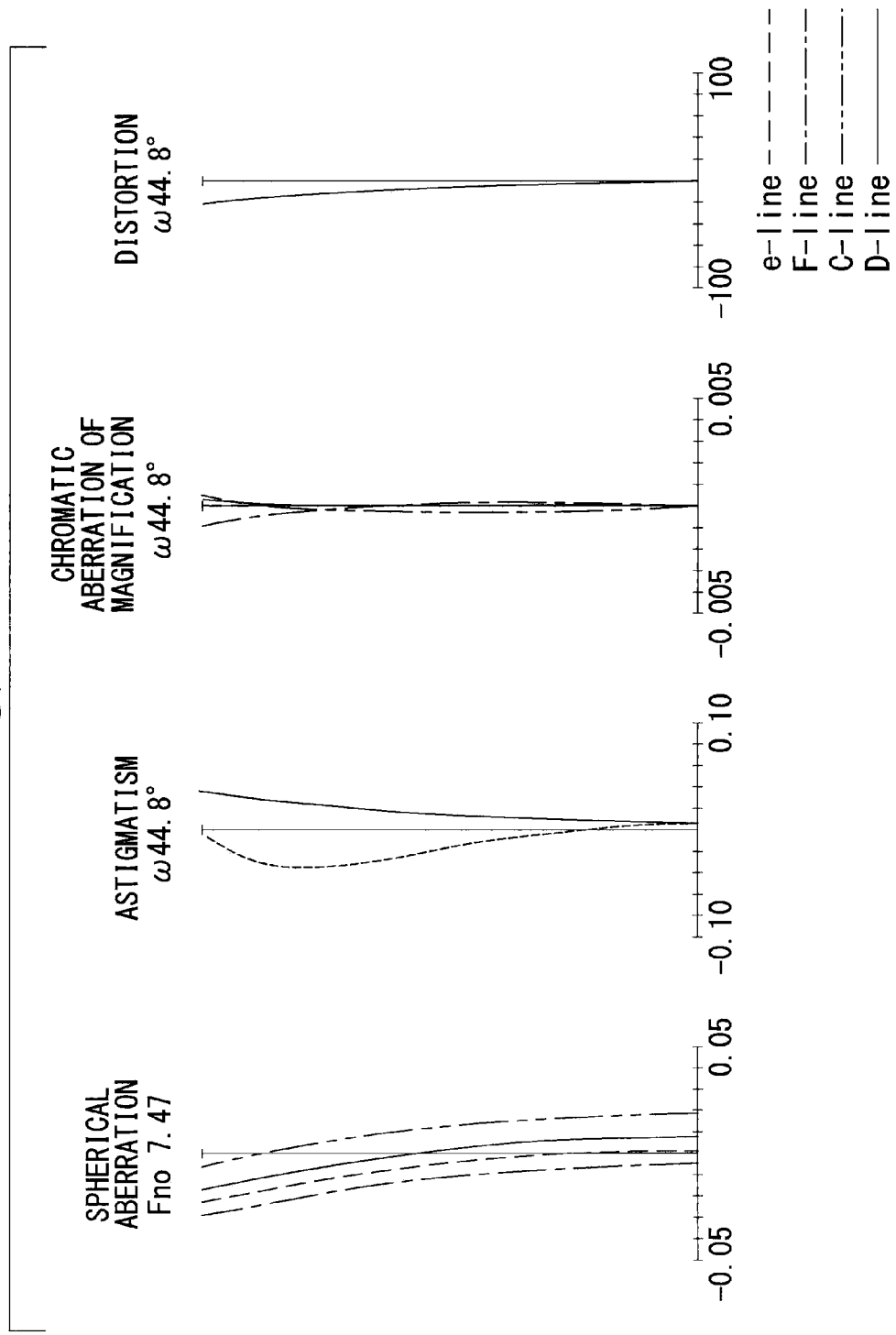
FIG. 22 shows aberration diagrams for the endoscope objective lens in the magnifying observation state shown in FIG. 20.

An endoscope objective lens 10 according to Reference Example 3 of the invention, as a reference example of the present invention, is shown in FIGS. 19 and 20. FIG. 19 shows the normal observation state, in which the second lens group 2 has been moved toward the object. FIG. 20 shows the magnifying observation state, in which the second lens group 2 has been moved toward the image. Furthermore, FIGS. 21 and 22 show spherical aberration, astigmatism, chromatic aberration of magnification, and distortion, corresponding to FIGS. 19 and 20, respectively. Furthermore, the endoscope objective lens 10 according to this example has the data shown in Tables 13, 14, and 15.

TABLE 13

| object surface | | $d_0$ | D0 | | | | |
|---|---|---|---|---|---|---|---|
| $r_1$ | ∞ | $d_1$ | 0.32 | $n_1$ | 1.88300 | $v_1$ | 40.76 |
| $r_2$ | 0.820 | $d_2$ | 0.37 | | | | |
| $r_3$ | ∞ | $d_3$ | 0.30 | $n_2$ | 1.52100 | $v_2$ | 65.13 |
| $r_4$ | ∞ | $d_4$ | 0.20 | | | | |
| $r_5$ | −1.072 | $d_5$ | 1.01 | $n_3$ | 1.69895 | $v_3$ | 30.13 |
| $r_6$ | −1.575 | $d_6$ | 0.03 | | | | |
| $r_7$ | 3.911 | $d_7$ | 0.86 | $n_4$ | 1.77250 | $v_4$ | 49.6 |
| $r_8$ | −1.695 | $d_8$ | 0.32 | $n_5$ | 1.92286 | $v_5$ | 18.9 |
| $r_9$ | −3.020 | $d_9$ | D9 | | | | |
| $r_{10}$ | ∞ | $d_{10}$ | 0.03 | | | | |
| $r_{11}$ | ∞ | $d_{11}$ | 0.30 | $n_6$ | 1.77250 | $v_6$ | 49.6 |
| $r_{12}$ | 1.301 | $d_{12}$ | 0.32 | $n_7$ | 1.59270 | $v_7$ | 35.31 |
| $r_{13}$ | ∞ | $d_{13}$ | D13 | | | | |
| $r_{14}$ | 3.887 | $d_{14}$ | 1.20 | $n_8$ | 1.48749 | $v_8$ | 70.23 |
| $r_{15}$ | −2.731 | $d_{15}$ | 0.05 | | | | |
| $r_{16}$ | 7.273 | $d_{16}$ | 0.91 | $n_9$ | 1.48749 | $v_9$ | 70.23 |
| $r_{17}$ | −1.748 | $d_{17}$ | 0.34 | $n_{10}$ | 1.92286 | $v_{10}$ | 18.9 |
| $r_{18}$ | −4.176 | $d_{18}$ | 0.25 | | | | |
| $r_{19}$ | ∞ | $d_{19}$ | 0.30 | $n_{11}$ | 1.52100 | $v_{11}$ | 65.13 |
| $r_{20}$ | ∞ | $d_{20}$ | 0.53 | | | | |
| $r_{21}$ | ∞ | $d_{21}$ | 0.70 | $n_{12}$ | 1.51633 | $v_{12}$ | 64.14 |
| $r_{22}$ | ∞ | $d_{22}$ | 0.70 | $n_{13}$ | 1.50510 | $v_{13}$ | 63.26 |

TABLE 14

| | normal observation state | magnifying observation state |
|---|---|---|
| D0 | 7.5 | 1.6 |
| D9 | 0.2 | 1.8 |
| D13 | 1.8 | 0.2 |
| $f_1$ | 0.97 | 1.14 |
| $F_{no}$ | 7.42 | 7.47 |

TABLE 15

| Conditional Expressions (1)~(5) | |
|---|---|
| $f_2/f_W$ | −7.47 |
| $|f_M/f_W|$ | 28.4 |
| $f_3/f_2$ | −0.43 |
| $f_2/f_1$ | −3.75 |
| $f_3/f_1$ | 1.63 |

In this example, because the endoscope objective lens 10 satisfies Conditional Expressions (1) to (5), manufacturing errors are suppressed, and the aberrations are successfully removed.

An illumination optical system may be configured as described below.

Figure 23:
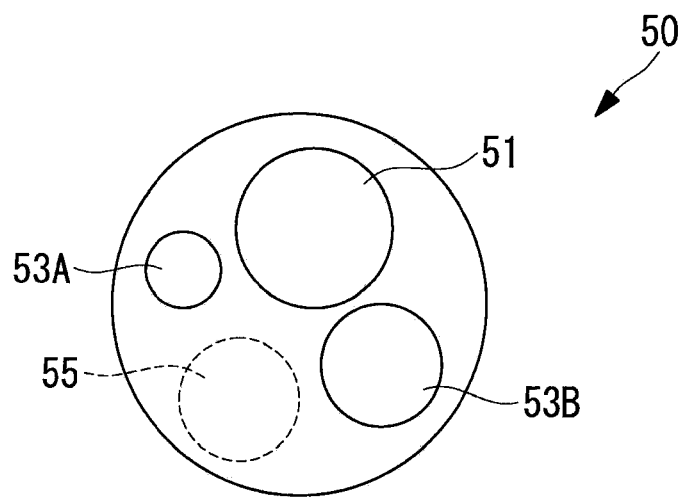
FIG. 23 is a sectional view of an endoscope scope.
Figure 24:
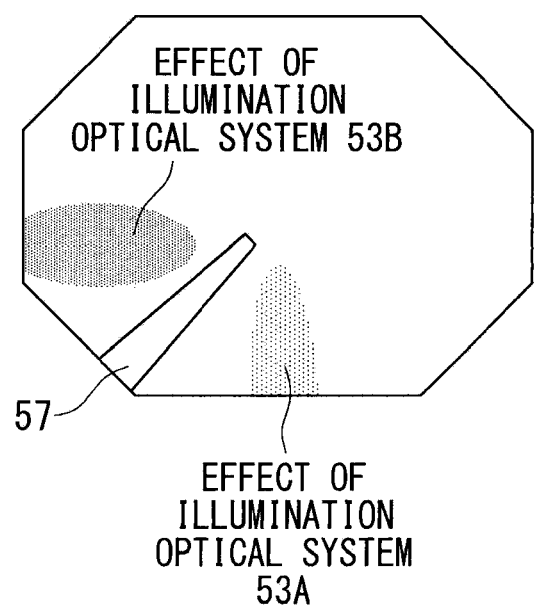
FIG. 24 is a view showing example shadows of forceps.

An endoscope scope 50 is configured as shown in FIG. 23, and an image acquisition optical system 51, illumination optical systems 53A and 53B, and a forceps channel 55 are provided therein. If the two illumination optical systems 53A and 53B are provided, as in the example shown in FIG. 23, when forceps 57 come out from the forceps channel 55, two shadows of the forceps 57 are cast, as shown in FIG. 24. At this time, if there is a difference between the levels of light emitted from the illumination optical systems 53A and 53B, one of the shadows is darker, which may make it difficult to view a lesion. If the ratio between the numbers of light guide members of these two illumination optical systems or the area ratio between tip lenses of the two illumination optical systems 53A and 53B becomes 2 or higher, the difference in darkness between the shadows makes the viewing difficulty more prominent. If this ratio is 2.6 or higher, viewing the lesion becomes very difficult.

At this time, the illumination optical systems 53A and 53B should be configured as described below.

Figure 25:
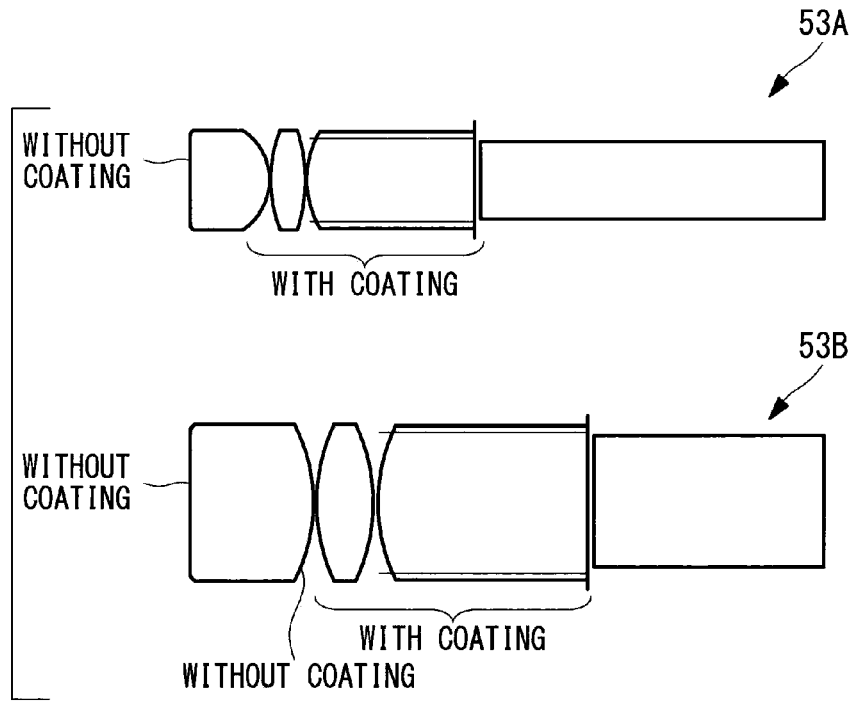
FIG. 25 is a view showing an example in which an antireflection coating is applied partially to two illumination optical systems.

It is preferred that an antireflection coating should not be applied to at least two surfaces in the illumination optical system that has a higher level of light, of the illumination optical systems 53A and 53B. For example, an antireflection coating is not applied to two surfaces in the illumination optical system 53B shown in FIG. 25. With this configuration, the level of light from the illumination optical system 53B, which has a higher level of light, is reduced, thus reducing the difference in darkness between the shadows of the forceps 57.

Figure 26:
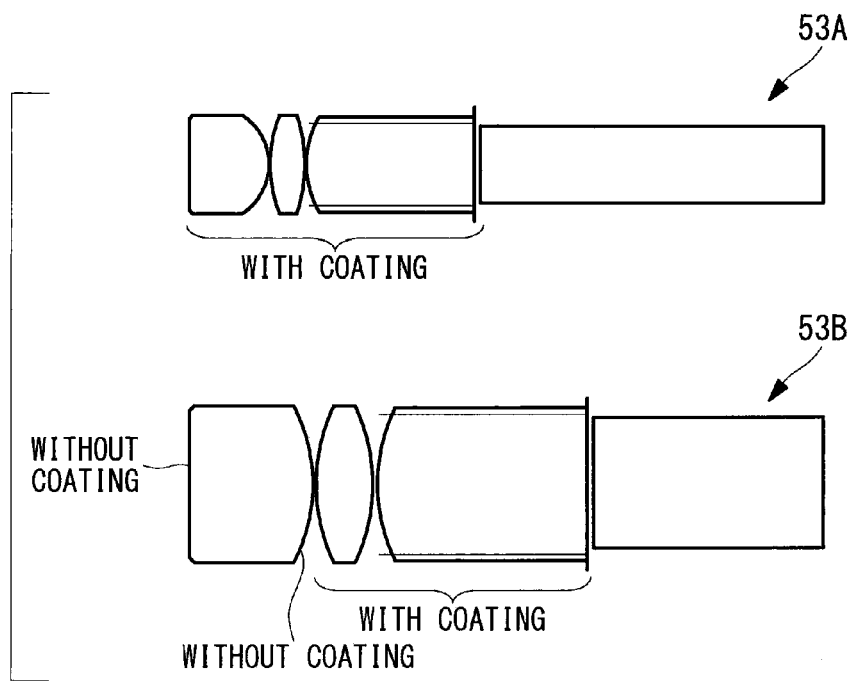
FIG. 26 is a view showing another example in which an antireflection coating is applied partially to the two illumination optical systems.

At this time, furthermore, it is more preferred that an antireflection coating should be applied to all surfaces in the illumination optical system that has a lower level of light. For example, an antireflection coating is applied to all surfaces in the illumination optical system 53A shown in FIG. 26. With this configuration, the level of light from the illumination optical system 53A, which has a lower level of light, is increased, thus further reducing the difference in darkness between the shadows of the forceps 57.

Figure 27:
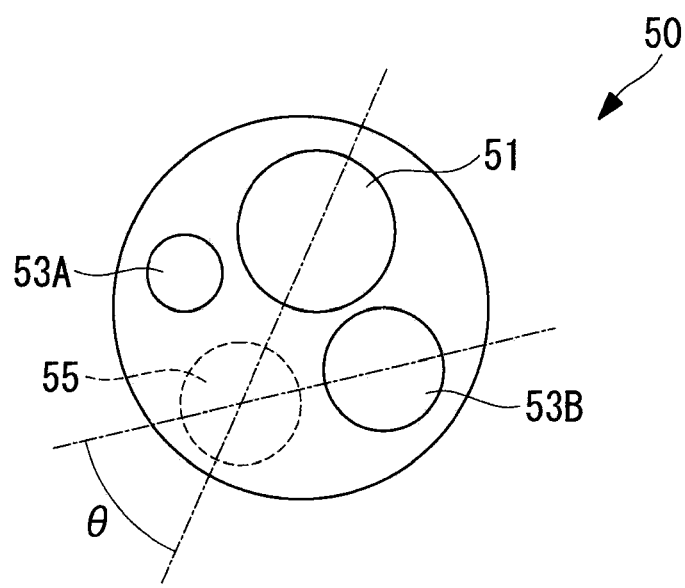
FIG. 27 is a view showing an example positional relationship between the illumination optical systems and a forceps channel.

Furthermore, the illumination optical systems and the forceps channel 55 should be positioned as described below. Specifically, as shown in FIG. 27, when the angle between a straight line connecting the center of the image acquisition optical system 51 and the center of the forceps channel 55 and a straight line connecting the center of the illumination optical system 53B, which has a higher level of light, and the center of the forceps channel 55 is θ, θ should be 60° or smaller.

Figure 28:
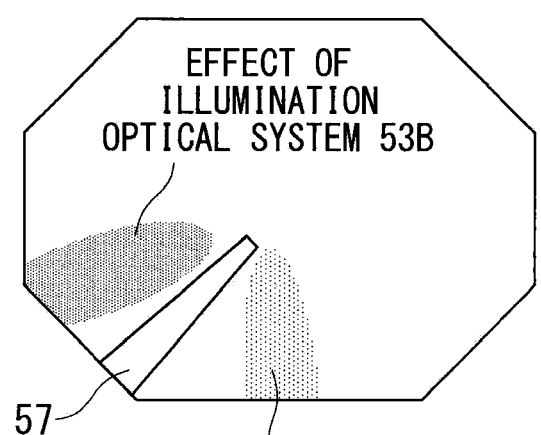
FIG. 28 is a view showing example shadows of the forceps cast by the endoscope scope shown in FIG. 27.

With this configuration, as shown in FIG. 28, the positions of the shadows of the forceps 57 cast by the illumination optical systems 53A and 53B come close to the forceps 57 themselves, thereby making it easy to observe the lesion.

With this configuration, it is possible to allow endoscopic observation that is less affected by the shadows of the forceps 57.

Furthermore, the lens tolerance may be set as described below.

Because lens manufacturing variations cause variations in the angle of view and the angular deviation, the angle of view and the angular deviation are adjusted for assembly, in some cases. In particular, the angle of view is adjusted by changing the gap between some lenses. Since the endoscope is a general wide-angle optical system, its basic configuration is a retrofocus type having a concave lens and a convex lens, in this order from the object side.

Therefore, the lens tolerance for adjusting the angle of view should be set as described below.

It is preferred that at least two lenses, i.e., an adjustment lens and a fixed lens, in this order from the object side, be provided, that the angle of view be adjusted by adjusting the gap therebetween, and that the eccentricity tolerance for the adjustment lens be set smaller than the eccentricity tolerance for the fixed lens.

The eccentricity tolerance is an acceptable value for an amount of shift between an axis with respect to the outer diameter of the lens and the lens optical axis.

Because the adjustment lens needs to be moved, a variation in shift eccentricity occurring at this time causes angular deviation. Therefore, it is desirable to reduce the eccentricity tolerance for shift. On the other hand, if the lens tolerance is set strictly, the cost is increased. Therefore, relaxing the lens tolerance for the fixed lens is desirable.

The adjustment lens should be a concave lens, and the fixed lens should be a convex lens.

Furthermore, it is effective to use those lenses for a wide-angle optical system whose half angle of view is about 80°.

Furthermore, it is desirable to satisfy the following conditional expression.

$$0.2 < \delta n/\delta p < 0.8$$

In the conditional expression, δn represents the eccentricity tolerance for the adjustment lens, and δp represents the eccentricity tolerance for the fixed lens.

If the value of δn/δp exceeds the upper limit of the conditional expression, the tolerance for the adjustment lens is too relaxed, thus causing an angular deviation, or the tolerance for the fixed lens is too strict, thus causing an increase in cost. On the other hand, if the value of δn/δp falls below the lower limit thereof, the tolerance for the adjustment lens is too strict, thus making it impossible to move the lens for adjustment, or the tolerance for the fixed lens is too relaxed, thus making it impossible to completely adjust the angular deviation.

Furthermore, it is desirable to satisfy the following conditional expression.

$$-0.6 < fn/fp < -0.2$$

In the conditional expression, fn represents the focal distance of the adjustment lens, and fp represents the focal distance of the fixed lens.

If the value of fn/fp exceeds the upper limit of the conditional expression, because the difference in power between the adjustment lens and the fixed lens is too large, the adjustment sensitivity is too strict, thus resulting in poor workability. If the value of fn/fp falls below the lower limit thereof, because the difference in power therebetween is too small, adjustment cannot be performed within an adjustment range.

With this configuration, it is possible to configure an imaging optical system in which cost and performance are well-balanced.

REFERENCE SIGNS LIST

1 first lens group
2 second lens group
3 third lens group
4 aperture stop
10 endoscope objective lens
11 concave lens
12 convex lens
13 meniscus lens

The invention claimed is:

1. An endoscope objective lens comprising, in order from an object side, a positive first lens group, a negative second lens group, and a positive third lens group,
  wherein the first lens group has only one meniscus lens; and
  a normal observation state (wide angle end) and a magnifying observation state (telephoto end) can be switched between by moving the second lens group on an optical axis, and the following conditions are satisfied;

$$-9 < f_2/f_W < -3.5 \tag{1}$$

$$4.5 < |f_M/f_W| < 8.3 \tag{2}$$

where $f_M$ represents a focal distance of the only one meniscus lens of the first lens group, $f_W$ represents an entire focal distance for the normal observation, and $f_2$ represents a focal distance of the second lens group;
  wherein the second lens group consists of a joined lens that is formed of a concave lens having a first refractive index and a convex lens having a second refractive index lower than the first refractive index; and a lens surface of the second lens group that is located closest to an object and a lens surface thereof that is located closest to an image each have a planar shape.

2. An endoscope objective lens according to claim 1, further comprising an aperture stop that is moved together with the second lens group.

3. An endoscope objective lens according to claim 2, satisfying the following conditional expression;

$$-0.77 < f_3/f_2 < -0.34 \tag{3}$$

where $f_3$ represents a focal distance of the third lens group.

4. An endoscope objective lens according to claim 2, satisfying the following conditional expression;

$$-4.5 < f_2/f_2 < -2.38 \tag{4}$$

where $f_1$ represents a focal distance of the first lens group.

5. An endoscope objective lens according to claim 2, satisfying the following conditional expression;

$$1.5 < f_3/f_1 < 2.5 \tag{5}.$$

* * * * *